US010870004B2

(12) United States Patent
Irazoqui et al.

(10) Patent No.: US 10,870,004 B2
(45) Date of Patent: *Dec. 22, 2020

(54) OPTICAL PRESSURE TREATMENT THROUGH ELECTRICAL STIMULATION

(71) Applicants: Purdue Research Foundation, West Lafayette, IN (US); The Jackson Laboratory, Bar Harbor, ME (US)

(72) Inventors: Pedro Irazoqui, Lafayette, IN (US); Simon John, Bar Harbor, ME (US); Alex Kokini, Lafayette, IN (US); Adam Willats, Columbus, IN (US); Alexander Chelminski, Jupiter, FL (US); Matt Matuscak, Pittsburgh, PA (US); Gabriel Simon, Miami Beach, FL (US)

(73) Assignees: Purdue Research Foundation, West Lafayette, IN (US); The Jackson Laboratory, Bar Harbor, ME (US)

( * ) Notice: Subject to any disclaimer, the term of this patent is extended or adjusted under 35 U.S.C. 154(b) by 190 days.

This patent is subject to a terminal disclaimer.

(21) Appl. No.: 16/101,040

(22) Filed: Aug. 10, 2018

(65) Prior Publication Data

US 2019/0001134 A1 Jan. 3, 2019

Related U.S. Application Data

(63) Continuation of application No. 14/565,129, filed on Dec. 9, 2014, now Pat. No. 10,493,274.
(Continued)

(51) Int. Cl.
*A61N 1/36* (2006.01)
*A61B 3/16* (2006.01)
*A61N 1/05* (2006.01)

(52) U.S. Cl.
CPC ............ *A61N 1/36046* (2013.01); *A61B 3/16* (2013.01); *A61N 1/3606* (2013.01); *A61N 1/0556* (2013.01)

(58) Field of Classification Search
CPC .................................................. A61N 1/36046
See application file for complete search history.

(56) References Cited

U.S. PATENT DOCUMENTS 4,271,841 A 6/1981 Friedman
4,603,697 A 8/1986 Kamerling
(Continued)

FOREIGN PATENT DOCUMENTS

WO WO 2005/072294 8/2005
WO WO 2009/150688 12/2009
(Continued)

OTHER PUBLICATIONS

Ahmed [online], "Addendum viii," Nov. 1993, [retrieved on Nov. 6, 2018], retrieved from: URL <https://www.accessdata.fda.gov/cdrh_docs/pdf/K925636.pdf>, 7 pages.
(Continued)

*Primary Examiner* — Michael W Kahelin
(74) *Attorney, Agent, or Firm* — Fish & Richardson P.C.

(57) ABSTRACT

An arrangement for reducing intraocular pressure includes a pulse signal source, a probe coupling, and at least one electrode. The probe coupling is configured to be supported on a portion of a living eye. The electrodes are supported on the probe coupling. The electrodes are operably coupled to receive a pulse signal from the pulse signal source.

20 Claims, 10 Drawing Sheets

Related U.S. Application Data

(60) Provisional application No. 61/913,883, filed on Dec. 9, 2013.

(56) References Cited

U.S. PATENT DOCUMENTS

| | | | |
|---|---|---|---|
| 4,614,193 | A | 9/1986 | Liss |
| 6,443,893 | B1 | 9/2002 | Schnakenberg |
| 7,282,046 | B2 | 10/2007 | Simon |
| 8,128,588 | B2 | 3/2012 | Coroneo |
| 8,267,882 | B2 | 9/2012 | Euteneuer et al. |
| 8,415,364 | B2 | 4/2013 | Epstein et al. |
| 8,419,673 | B2 | 4/2013 | Rickard |
| 2002/0013545 | A1 | 1/2002 | Soltanpour et al. |
| 2006/0224215 | A1 | 10/2006 | Pattern et al. |
| 2007/0027537 | A1 | 2/2007 | Castillejos |
| 2007/0282405 | A1 | 12/2007 | Wong et al. |
| 2007/0284205 | A1 | 12/2007 | Wong et al. |
| 2011/0022118 | A1 | 1/2011 | Rickard |
| 2013/0030415 | A1 | 1/2013 | Britt |
| 2013/0941153 | | 7/2013 | Irazoqui et al. |
| 2014/0031905 | A1 | 1/2014 | Irazoqui et al. |
| 2014/0213843 | A1 | 7/2014 | Pilla et al. |
| 2017/0007834 | A1 | 1/2017 | Pedro et al. |

FOREIGN PATENT DOCUMENTS

| | | |
|---|---|---|
| WO | WO 2013/063111 | 5/2013 |
| WO | WO 2015/157725 | 10/2015 |

OTHER PUBLICATIONS

Braendstrup [online], "Muscular bio stimulator (2nd version)," 2011, May, available: http://www.redcircuits.com/Page124.htm.

Chandler, "Key needs and opportunities for treating glaucoma," Investigative Ophthalmology and Visual Science, May 2012, vol. 53, pp. 2456-2460.

Constable & Lim, Color Atlas of Ophthalmology. World Scientific Publishing Company, 1995.

DeLuca, "Draft guidance for industry and fda staff: Class ii special controls guidance document: Powered muscle stimulator for rehabilitation," CDRH, Apr. 5, 2010, 19 pages.

Dietlein, "The medical and surgical treatment of glaucoma," Dtsch Arztebl Int, 2009, vol. 116, pp. 597-606.

FDA [online], "Tomey dtl electrode," May 1997, [retrieved on Nov. 6, 2018], retrieved from: URL <https://www.accessdata.fda.gov/scripts/cdrh/cfdocs/cfPMN/pmn.cfm?ID=K961805>, 1 page.

FDA, "Guidance for industry and for fda reviewers/staff-guidance on 510(k) submissions for keratoprostheses," Mar. 1999, 11 pages.

Foster[online], "Specific questions related to glaucoma," available on or before Oct. 7, 2013, via Internet Archive: Wayback Machine Url : <https ://web.archive.org/web/20131007014544/http://www.rcophth.ac.uk/page.asp?section=373&sectionTitle=Specific+Questions+Related+to+Glaucoma>, [retrieved on Nov. 6, 2018], retrieved from: URL <http://www.rcophth.ac.uk/page.asp?section=373&sectionTitle=Specific+Questions+Related+to+Glaucoma>, 1 page.

G. R. Foundation [online], "Glaucoma facts and stats," Aug. 2013, [retrieved on Nov. 5, 2018], retrieved from: <http://www.glaucoma.org/glaucoma/glaucoma-facts-and-stats.php>, 3 pages.

G. Technologies [online], "Sd9 square pulse stimulator," available on or before Jul. 7, 2013, via iInternet Archive: Wayback Machine URL <https://web.archive.org/web/20130707155649/http://www.grasstechnologies.com/products/stimulators/stimsd9.html>, [retrieved Nov. 6, 2018], retrieved from: URL <http://www.grasstechnologies.com/products/stimulators/stimsd9.html>, 2 pages.

Ghosh et al.,"Lens-solution interactions: Impact on biocompatibility," Presented at the 15th Symposium on the Material Science and Chemistry of Contact Lenses. Center for Devices and Radiological Health, FDA, Mar. 18, 2011, 43 pages.

Glaucoma Research Foundation [online], "Laser surgery," Aug. 25, 2017, [retrieved on Nov. 6, 2018], retrieved from: URL <http://www.glaucoma.org/treatment/laser-surgery.php>, 3 pages.

Greenwell and Spillman, "Use of medicated drops and oral tablets in glaucoma treatment," Curr Opin Ophthalmol., Apr. 1996, vol. 7, pp. 44-46.

Fechter, "Improvised 3-0 polypropylene plug for the glaucoma drainage tube during phacoemulsification," Ophthalmic Surg. Lasers Imaging, Jan./Feb. 2008, vol. 39, pp. 86-87.

Janunts, "Optical remote sensing of intraocular pressure by an implantable nanostructured array," available: http://www.uniklinikum-saarland.de/en/facilities/departments and institutes/experimental ophthalmology/research/iop sensing.

John M. Eisenberg Center for Clinical Decisions and Communications Science, "Comparisons of medical, laser, and incisional surgical treatments for open-angle glaucoma in adults," AHRQ, 2012, 4 pages.

Keenan, [online], "510(k) summary," Nov. 28, 2008, [retrieved on Nov. 6, 2018], retrieved from: URL <https://www.accessdata.fda.gov/cdrh_docs/pdf8/K082011.pdf>. 7 pages.

King et al, Clinical review: Glaucoma, BMJ, Jun. 15, 2013, vol. 346, pp. 29-33.

Kobayashi et al, "Accuracy of intraocular pressure by tono-pen xl over amniotic membrane patching in rabbits," American Journal of Ophthalmology, Apr. 2003, vol. 135, pp. 536-537.

Kok & Barton, "Uveitic glaucoma," Ophthalmol Clin North Am, vol. 15, pp. 375-387, 2002.

Lee et al, "Primary acute angle closure: long-term clinical outcomes over a 10 year period in the chinese population," Apr. 2014, vol. 34, pp. 165-169.

Lu et al, "Electrical stimulation with a penetrating optic nerve electrode array elicits visuotopic cortical responses in cats." J Neural Eng, Jun. 2013, vol. 10, pp. 1-11.

Lusby et al [online], "Glaucoma," Sep. 2011, [retrieved on Nov. 5, 2018], retrieved from: <http://www.nlm.nih.gov/medlineplus/ency/article/001620.htm>, 8 pages.

Lweinstein et al, "Antibacterial properties of aged dental cements evaluated by direct-contact and agar diffusion tests," Journal of Prosthetic Dentistry, Apr. 2005, vol. 93, pp. 364-371.

M. Detry-Morel, "Side effects of glaucoma medications," Bull. Soc. Belge Ophthal, 2006, vol. 299, pp. 27-40.

M. Shields, Shields textbook of glaucoma. Philadelphia, PA: Lippincott Williams & Wilkins, 2005.

Managed Care Eye Institute [online], "Coats of the eye: Ciliary body," Jan. 2012, [retrieved on Nov. 5, 2018], retrieved from: <http://teaching.pharmacy.umn.edu/courses/eyeAP/Eye_Anatomy/CoatsoftheEye/CiliaryBody.htm>, 1 page.

Mayo Clinic Staff [online], "Glaucoma: Treatment and drugs," Oct. 2012, available: [retrieved on Nov. 5, 2018], retrieved from <:www.mayoclinic.com/health/glaucoma/DS00283/DSECTION=treatments-and-drugs>, 5 pages.

Mountaintop Medical, "Advances in opthamology: Markets in the treatment of eye disorders and corrective vision," Jul. 2009.

Murgatroyd & Bembridge, "Intraocular pressure," Oxford Journal of Medicine, 2008, vol. 8, pp. 100-103.

Nesterov & Khadikova [online], "Effect of ciliary muscle electrical stimulation on ocular hydrodynamics and visual function in patients with glaucoma," Vestn Oftalmol., 1997, vol. 113, pp. 12-14 [English Abstract].

Optonol Ltd [online], "Summary of safety & effectiveness," Mar. 1, 2003, [retrieved on Nov. 6, 2018], retrieved from: URL <https://www.accessdata.fda.gov/cdrh_docs/pdf3/K030350.pdf>, 5 pages.

Optonol Ltd. [online], "510(k) summary," Mar. 2002, [retrieved on Nov. 6, 2018], retreived from: URL <https://www.accessdata.fda.gov/cdrh_docs/pdf/K012852.pdf>, 7 pages.

Panarelli et al, "Scleral stula closure at the time of glaucoma drainage device tube repositioning: a novel technique," Arch Ophthalmol , Nov. 2012, vol. 130, pp. 1447-1451.

Pescosolido et al, "Role of dopaminergic receptors in glaucomatous disease modulation," Biomed. Res. Int., 2013, 5 pages.

Porcari et al, "Effects of electrical muscle stimulation on body composition, muscle strength, and ssearance," Journal of Strength and Conditioning Research, 2002, vol. 16, pp. 165-172.

(56) References Cited

OTHER PUBLICATIONS

Quigley & Vitale, "Models of open-angle glaucoma prevalence and incidence in the United States," Investigative Ophthalmology and Visual Science, Jan. 1997, vol. 38, pp. 83-91.
Fernandes et al, "Artificial vision through neuronal stimulation," Neuroscience Letters, Jun. 25, 2012, vol. 519, pp. 122-128.
Moorthy, "Glaucoma associated with uveitis," Surv Ophthalmol, 1997, pp. 361-394.
Sjogren and Dahl, "Cytotoxicity of dental alloys, metals, and ceramics assessed by millipore filter, agar overlay, and mtt tests," Elsevier, Aug. 2000, vol. 84, pp. 229-236.
Sun et al, "Spatiotemporal properties of multipeaked electrically evoked potentials elicited by penetrative optic nerve stimulation in rabbits," Investigative Ophthalmology and Visual Science, Aug. 2010, vol. 52, pp. 146-154.
Texas Instruments, "Lm741 operational amplifier," Mar. 2013, 11 pages.
U. Z. Leuven [online], Validation of retinal oximetry in glaucoma patients: a structural and functional correlation, Feb. 2013 [retrieved on Nov. 5, 2018], retrieved from: <http://www.clinicaltrials.gov/ct2/show/NCT01391247?term=glaucoma&rank=13>, 6 pages.
US Food and Drug Administration [online], "Classify your medical device," Dec. 2012, available on or before Apr. 17, 2018, via Internet Archive: Wayback Machine URL: <https://web.archive.org/web/20180417153853/http://www.fda.gov/MedicalDevices/DeviceRegulationandGuidance/Overview/ClassifyYourDevice/>, [retreived on Nov. 6, 2018], retrieved from: URL <http://www.fda.gov/MedicalDevices/DeviceRegulationandGuidance/Overview/ClassifyYourDevice/>, 3 pages.
V. E. S. Center [online], "Ahmed valve glaucoma implant with adjunctive subconjunctival bevacizumab in refractory glaucoma," May 2010, available: http://www.clinicaltrials.gov/ct2/show/NCT01128699?term=glaucoma&rank=15>, 6 pages.
Valk, "Intraocular pressure-lowering effects of all commonly used glaucoma drugs: a meta-analysis of randomized clinical trials," Ophthalmology, 2005, vol. 112, pp. 1177-1185.
Wang et al, "Intervention of laser periphery iridectomy to posterior iris bowing in high myopic eyes," Chin. Med. J. (Engl)., Dec. 2012, vol. 125, pp. 4466-4469.
Wong & Graham, "Effect of repeat use and coating defects of gold foil electrodes on electroretinogram recording," Vision Research, 1995, vol. 35, pp. 2795-2799.
Pham & Hu, "Cytotoxicity evaluation of multipurpose contact lens solutions using an in vitro test battery," CLAO Journal, Jan. 1999, vol. 25.
EP Supplementary Partial European Search Report in European Appln. No. 17816256, dated Jun. 14, 2019, 16 pages.
PCT International Search Report and Written Opinion in International Appln. No. PCT/US2017/038879, dated Sep. 27, 2017, 15 pages.

OPTICAL PRESSURE TREATMENT THROUGH ELECTRICAL STIMULATION

This application is a continuation of U.S. application Ser. No. 14/565,129, filed Dec. 9, 2014, which claims the benefit of U.S. Provisional Patent Application Ser. No. 61/913,883, filed Dec. 9, 2013, which are incorporated herein by reference in their entirety.

FIELD OF THE INVENTION

The invention relates generally to methods and apparatus for treatment of glaucoma and other ocular pressure-related conditions in a living being.

BACKGROUND

Glaucoma is a term which refers to a family of conditions which cause optic nerve damage. Glaucoma is currently the leading cause of blindness and continues to cause blindness in around 10% of even those patients who receive the most up to date treatment [1]. There are currently strategies for managing Glaucoma including eye drops and surgeries, but often the eye drops can cause problems ranging from eye irritation to severe heart problems [2]. The surgeries used to treat glaucoma are often successful, but bring the usual surgical risks, and often treat the problem only for a short time.

What scientists now believe causes the most prevalent type of glaucoma is an excess of intraocular pressure (IOP) which presses on, then damages the optic nerve [2]. Fluid is pumped into the anterior chamber of the eye to, among other things, clean the lens. The fluid and is then drained out through the drainage tissues at the junction of the cornea and iris in the region of the eye known as the limbus [3]. An excess of the aqueous humor in the eye could be caused by a combination of the ciliary body producing too much fluid, or too much resistance to aqueous humor drainage out of the eye. Existing medical and surgical treatments reduce IOP to non-damaging levels by targeting either the drainage or production of aqueous humor Current treatment methods for reducing intraocular pressure in glaucoma patients incur unacceptable side effects or provide only temporary relief of symptoms for the chronic disease [2]. There is a need to develop a method to permanently reduce the intraocular pressure in the eye of all patients with glaucoma to a normal level (15.5 mmHg) without causing unacceptable side effects [4].

This book chapter describes what glaucoma is and the two different glaucoma types, open-angle and closed-angle glaucoma. It also describes the necessary treatments for patients suffering from glaucoma. This provides a good starting source for learning the basics of glaucoma. [7]

This article explains normal and abnormal operating conditions of the eye with respect to the intraocular pressure. The steady state operations of the IOP is detailed at 10-20 mmHg. This also explores into what determines the IOP levels and what can disrupt the normal pressure. This entry details routine dynamics of the fluid production and flow. It also tells how various conditions and stimuli can affect the IOP.[8]

This study uses electrical stimulation on the ciliary muscle. These researchers found using pulses up to 15 ms long with a current amplitude up to 10 mA for three to seven minutes using a lens with four electrodes placed on the eyeball. Gradual improvements visual and hydrodynamic parameters were seen by the end of the follow-up in six months. After ten sessions on transscleral stimulation IOP decreased by 16%. [9]

This patent puts forth a method to prevent presbyopia and glaucoma through ciliary body stimulation. This method uses low-voltage dc pulses transmitted to the ciliary body though electrodes attached to lenses placed over both eyes. The lenses are set 2-5 mm from the corneal limbus. [10]

This source is a patent for a system that can be used to treat ocular misalignment. The treatment is using electrical stimulation of ocular recti using an implantable unit. The stimulation signal is a periodically interrupted train of pulses, with 50 to 100 pulses per minute. [11]

This patent provides a system for treating open angle glaucoma and presbyopia through electrical stimulation of the ciliary muscle. This implant used delivers signals to the ciliary muscle that widens the interbecular spaces to facilitate outflow of aqueous fluid from the eye and widens the lense, thereby lowering IOP. [12]

Within the eye, there is a smooth-muscle tissue called the ciliary muscle, which is part of the ciliary body. It has two different orientations of the muscle with separate functions. The circular muscle tissue controls the shape of the lens in the eye. Changing the shape of the lens changes the focus of the eye so that the image will always be clear on the back of the retina. The longitudinal muscle tissue controls the configuration of the trabecular meshwork. The aqueous humor is secreted by the ciliary body. It is secreted into the posterior chamber of the eye between the iris and lens. It washes over the lens and then moves through the pupil into the anterior chamber. Ultimately, much of the aqueous humor leaves the eye through the trabecular meshwork and Schlemm's canal drainage tissues. Some aqueous humor leaves the eye through the uveoscleral drainage pathway, a process that is also modulated by the ciliary muscle. Aqueous humor production, flow and drainage are important for nourishing the front of the eye, removing metabolites and normal vision.

In a patient with glaucoma, the aqueous humor builds up in the eye. This can be due to the blocking or a slowing of the drainage of the aqueous humor in the trabecular meshwork. As the excess fluid builds in the eye, it increases the intraocular pressure. As this pressure increases, it causes the optic nerve to get damaged. If left untreated, the pressure does so much damage to the optic nerve that it will eventually lead to blindness [13].

There are actually multiple types of glaucoma. Open-Angle glaucoma is where the aqueous humor does not drain as quickly due to abnormal resistance in the trabecular meshwork and Schlemm's canal pathway. The increase in pressure is usually a slow process. Angle-Closure glaucoma is where the aqueous humor does not drain from the eye because of a sudden blockage of the trabecular network by the iris. This causes a sudden spike in the intraocular pressure and is considered an emergency. Congenital glaucoma is a birth defect caused by abnormal eye development. Secondary glaucoma is caused by external factors such as drugs, disease, or trauma. Open-Angle glaucoma is the most common form of glaucoma and has a clear genetic component [13].

Symptoms vary depending on the type of glaucoma. Open-angle glaucoma generally does not exhibit any symptoms. When vision starts to decrease, severe damage has already been done to the optic nerve. Angle-close glaucoma has symptoms such as eye pain, clouded vision, nausea, rainbow halos around lights, and red or swollen eyes. Congenital glaucoma may go unnoticed for a while. A child may get cloudy eyes, an enlargement of one or both eyes, red eye, sensitivity to light, or tearing [13].

As one of the most prevalent causes of blindness across the globe, glaucoma affects around 60.5 million people (as of 2010) [14] with an incidence of 7 million new cases each year (as of 2009). Within the U.S. open-angle glaucoma, the most common subtype in the glaucoma family affects around 2.5 million people [15]. The populations of patients with glaucoma or high IOP (ocular hypertension, OHT) are both predicted to grow steadily over the next several years. From FIGS. 8 and 9 it can be seen that by 2016 the prevalences are expected to be 3.1 million and 5.0 million for glaucoma and OHT respectively, with compound annual growth rates of about 1.6% for both populations. From this analysis it is attractive to target the IOP regulating therapy to the OHT population as well as the traditional glaucoma population.

The cost of pharmaceutical treatment of glaucoma has been thoroughly studied revealing that even generic medications create a cost issue in the treatment.

Other costs associated with glaucoma include surgeries, doctors appointments, procedures and especially loss of vision all result in loss of productivity for patients due to absenteeism. One study estimates this cost to the economy to be greater than $3 billion [15]. This cost has potential to be recovered by a more effective way of monitoring and treating glaucoma.

The new technologies being developed include both methods in identifying and treating patients with glaucoma. There is new research on using oximetry to determine if there are differences between the oxygen content in the eye of patients with glaucoma compared to patients without glaucoma [21]. Our design is used as a treatment for glaucoma while this research is to try and identify patients with glaucoma so there is no conflict with our design.

Emerging technology can be found in ways to treat glaucoma. There is research on using an injection of bevacizumab after implanting a valve in the eye to try and improve the efficacy of the implant. Bevacizumab is a drug that decreases vascular endothelial growth factor-A. By injecting the drug into the eye after an implant they hope to decrease the scar tissue that forms after the surgery to avoid a fibrous capsule forming around the implant. There is also research on using statins as a treatment for glaucoma [22]. These statins inhibit HMG-CoA reductase catalyzed transformation of HMG-CoA to mevalonic acid. Another drug treatment method for glaucoma is the use of thrombin-derived peptides [23]. Our design does not use drugs to treat glaucoma so there is no conflict with our design.

There are also several different patents for implants and devices to treat glaucoma. There is a design for a new tube to be used as a valve to improve the drainage system as a treatment for open-angle glaucoma. This is designed to better allow fluid flow through the implant and into Schlemm's canal [24]. The design can be seen in FIG. 1.

Another implant is a plate designed to treat angle-closure glaucoma by placing the plate partially in Schlemm's canal. This design tried to correct the errors in other implants for angle-closure glaucoma by allowing good flow into Schlemm's canal and also keeping the surrounding tissue around the implant safe from high flow rates [25]. A drawing of this plate can be seen in FIG. 2.

A new idea is to use a pump in conjunction with an implanted valve to aid in the removal of the aqueous humor. This would increase the outflow of the fluid. Reverse flow of the fluid is prevented by using one-way valves [26]. FIG. 3 shows a diagram of this idea.

There is also a patent on a device that aids in trabeculotomy surgeries. This device includes a footplate to penetrate into Schlemm's canal, an infusion system to allow fluid to flow out to a collection plate during the surgery, and an aspiration system to remove tissue or bubbles and is directly connected to the cutting blade or other tissue removal system [26]. A drawing of the device can be seen in FIG. 4.

Another design is for scleral implants that aid in the drainage of the aqueous humor. This implant purportedly relieves intraocular pressure by exerting an outward pressure on the sclera to restore proper outflow of the aqueous humor. It also allows for a drug delivery system not provided in other ocular implants [27]. FIG. 5 shows a drawing of these scleral implants.

These ideas are improvements on existing methods of treating and all have an intraocular component. Nevertheless, there remains a need for cost effective strategies for the treatment of glaucoma. A big gap in the current solutions is for a treatment that is relatively low risk but also convenient for the patient. What exists now are solutions that are either low risk (topical agents) or convenient for the patient long-term (surgery), but not both. There is also a need for a method that is more biocompatible with the eye and has less side effects. Almost all of the current treatments result in a chance of some mild to serious side effects. This risk becomes increasingly acceptable for a patient as they come closer to blindness, but an ideal solution will provide relief of elevated IOP with minimal to no side effects. Finally, the current treatments have little adjustability for treating patients individually and none have feedback mechanisms based on IOP.

Current pharmacological and surgical methods for reducing intraocular pressure in glaucoma and ocular hypertensive patients present high risk of complications or provide only acute relief of symptoms for the chronic disease.

There is a need to develop a method to chronically reduce IOP of all patients with glaucoma or ocular hypertension to a normal level without causing unacceptable side effects.

While many surgical and chemical solutions exist, the other categories are mainly filled with solutions that are not currently on the market. The two biggest approaches to glaucoma treatment at the moment are surgeries to open channels in the eye, or eye drops to regulate fluid flow, and other types of intervention (i.e. electrical, or implanted devices) have not yet successfully been brought to market. This suggests that a solution from one of these other areas has the potential to avoid some of the limitations of current glaucoma treatment (i.e. the need for repeated surgeries, or the unacceptable side effects of eye drops [38]).

Current pharmacological and surgical methods for reducing intraocular pressure in glaucoma and ocular hypertensive patients present risk of complications or provide only temporary relief of symptoms for the chronic disease.

There is a need to develop a method to chronically reduce IOP of all patients with glaucoma or ocular hypertension to a safe level without causing unacceptable side effects.

SUMMARY

At least some embodiments of the present invention use stimulation of the various nerves of the eye (such as the optic nerve and those associated with the ciliary muscle, such as the ciliary ganglion and ciliary nerves) to reduce and regulate intraocular pressure (IOP) to be used in Glaucoma intervention. The stimulation device consists of micro-controller which adjusts the amplitude and duration of the pulses used to stimulate the nerve. These pulses are then generated within the printed circuit board (PCB) and transmitted into the ring electrodes placed on the surface of the eye. The PCB and microcontroller are encased in a plastic enclosure external to the animal.

This simulator will also be integrated with an implantable IOP sensor to form a closed loop regulation system.

A first embodiment of the invention is an arrangement for reducing intraocular pressure that includes a pulse signal source, a probe coupling, and at least one electrode. The probe coupling is configured to be supported on a portion of a living eye. The electrodes are supported on the probe coupling. The electrodes are operably coupled to receive a pulse signal from the pulse signal source.

A second embodiment of the invention is a method of reducing intraocular pressure that includes providing an electrical signal to an interior portion of an eye of living being, measuring intraocular pressure in the eye, controlling the electrical signal based on the measured intraocular pressure.

Another embodiment is an arrangement for reducing intraocular pressure that includes an electrical signal source, at least one electrode, and an intraocular pressure sensor. The electrodes are operably coupled to receive an electrical signal from the electrical signal source. The electrodes are configured to be attached to a portion of an eye of a living being. The intraocular pressure measurement unit disposed proximate the eye and configured to generate an intraocular pressure measurement for the eye. The electrical signal source is operably coupled to receive the intraocular pressure measurement and is further configured to control the electrical signal based on the intraocular pressure measurement.

Current treatment uses chemical or surgical routes to try to change the flow into or out of the eye, whereas our technology takes advantage of electrical stimulation to regulate activity. Electrical stimulation is currently used to treat problems from muscle pain to epilepsy, however it has yet to be applied to IOP regulation. Our technology seeks to avoid the side-effects which eye drops might cause, and reduce the need for repeated surgeries caused by traditional surgical intervention. Electrical stimulation also has the advantage of being easily adjusted. Furthermore, by implementing this system with an implantable IOP measuring device the whole system could be closed-loop meaning it could correct and adjust the levels of stimulation itself to constant optimize therapy.

DETAILED DESCRIPTION

At least some embodiments of the present invention use electrical stimulation to modulate intraocular pressure in the eye. Electrical stimulation has been observed on other muscle groups on subjects at a variety of ages. By utilizing electrical muscle stimulation devices the researchers have been able to increase muscular strength, decrease body weight and body fat, and improve the firmness and tone in their subjects. [5] Another study discloses a circuit that circuit provides a low frequency stimulation (around 100 Hz) and a voltage up to about 50V. Included in this is variable pulse rate, width, and amplitude. [6]

Figure 1:
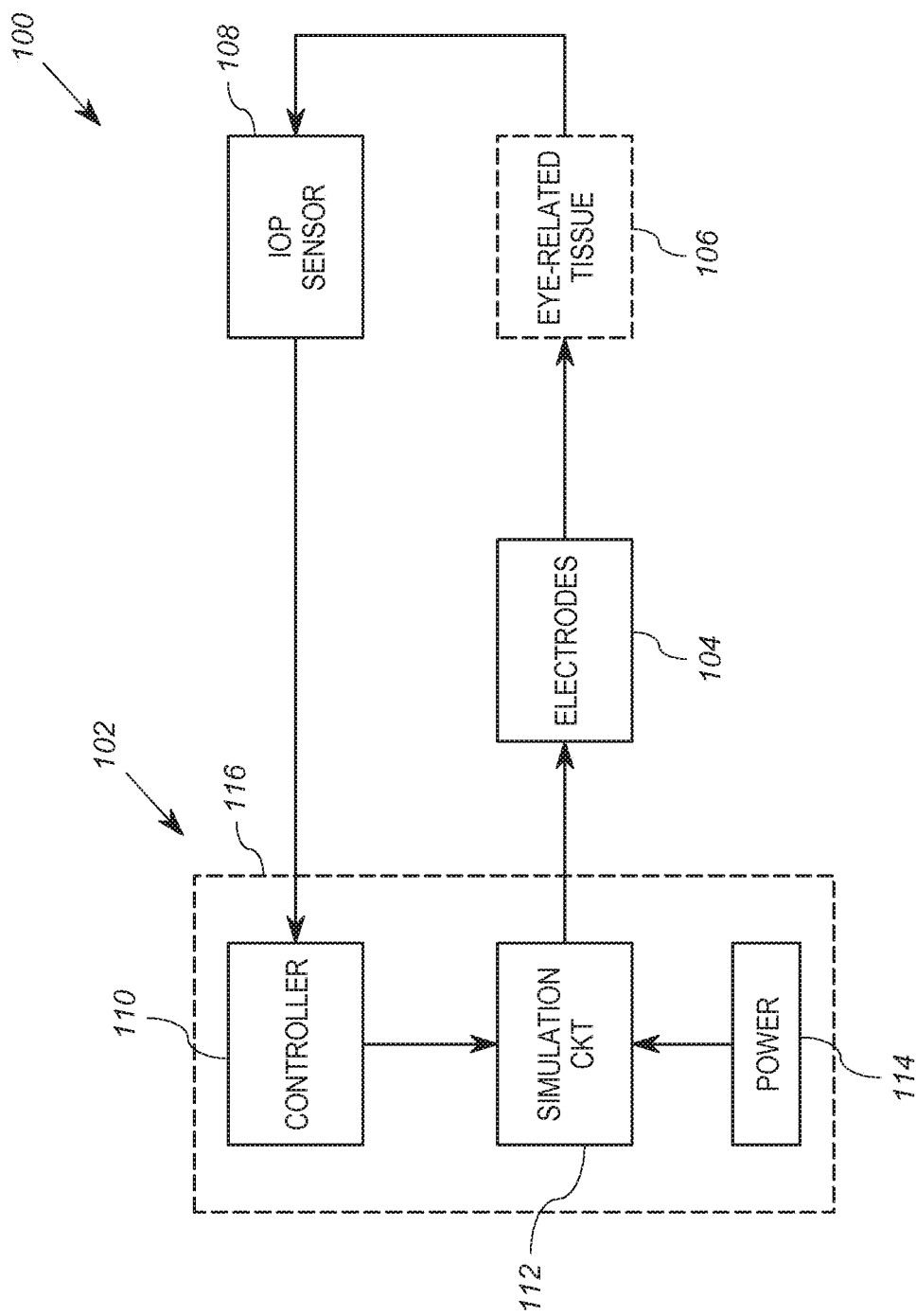
FIG. 1 shows a schematic block diagram of an exemplary arrangement for modulating intraocular pressure according to a first embodiment of the invention.

FIG. 1 shows a block diagram of a first embodiment of an arrangement 100 for reducing intraocular pressure that includes an electrical signal source 102, at least one electrode 104, and a intraocular pressure measurement or IOP sensor 108. The arrangement 100 is shown in context operably coupled to eye-related tissue 106. The electrical signal source 102 is a circuit or group of circuits that is operably coupled to receive an intraocular pressure measurement from the IOP sensor 108 and is configured to generate a controlled electrical signal based on the intraocular pressure measurement. The at least one electrode 104 is operably coupled to receive the electrical signal from the electrical signal source, and configured to be attached to a portion of an eye or eye-related tissue 106 of a living being. The IOP sensor is disposed proximate the eye-related tissue 106 and is configured to sense and generate the intraocular pressure measurement for the eye-related tissue 106.

In the embodiment of FIG. 1, the electrical signal source 102 comprises a controller 110, a stimulation circuit 112, and a power source 114. In at least some embodiments, the electrical signal source 102 includes a hermetically sealed enclosure 116 to allow implantation. In this embodiment the controller 110 may suitably be a microcontroller that is operably coupled to receive a value representative of the measured IOP from the IOP sensor 108, and is configured to selectively cause the stimulation circuit 112 to generate (or not generate) the electrical stimulation signals based on whether the value representative of the measured IOP is above a threshold. The threshold represents a value of IOP above which electrical stimulation is deemed necessary or at least beneficial for the purpose of reducing the IOP. Thus, the controller 110 is configured to cause the stimulation circuit 112 to generate the stimulation signals responsive to the IOP measurement value exceeding the threshold, and to cause the stimulation circuit 112 to stop generating the stimulation signals when the IOP measurement falls below the threshold, or falls below a second, lower threshold (to allow for hysteresis). In this manner, the controller 110 is configured to cause application of electrical stimulation to the eye tissue 106 only when the IOP becomes excessively high.

In some embodiments, the controller 110 may suitably be configured to also cause the stimulation circuit 112 to provide stimulation signals when the measured IOP value falls below a threshold value, and to stop the stimulation signals when the measure IOP value exceeds that threshold, or another, higher threshold (to allow for hysteresis).

In general, to cause the stimulation circuit 112 to selectively provide or not provide stimulation signals, the controller 110 is operably coupled to provide control signals to the stimulation circuit 112. In some cases, the control signals further include signals that control the amplitude, pulse frequency, and/or pulse width of the stimulation signals generated by the stimulation circuit 112.

Figure 2:
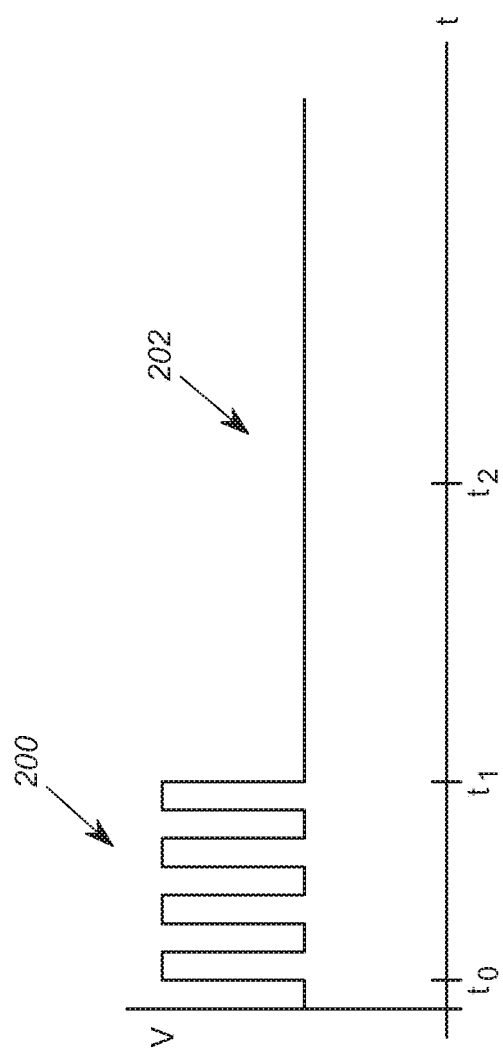
FIG. 2 shows a timing diagram of a stimulation signal that may be selectively applied in accordance with embodiments of the present invention.

The stimulation circuit 112 is a circuit that is configured to receive control signals from the controller 110 and generate electrical stimulation signals therefrom. In general, the stimulation circuit 112 produces stimulation signals in the form of electrical pulses in a pulse train, or pulse burst. FIG. 2, for example shows a timing diagram of an output voltage generated by the stimulation circuit 112 that includes an exemplary stimulation signal 200 and a no signal output 202. The stimulation signal 200 lasts from a time to to a time $t_1$, and no signal is produced from the time $t_1$ through and beyond the time $t_2$. As discussed above, the control signals from the controller determine when the signal 200 is produced and when no signal 202 is produced.

As also discussed above, the pulse frequency, pulse width and amplitude may be varied. The stimulation circuit 112 may suitably be configured for manual adjustment of such values or automatic adjustment of the values via the controller 110.

Figure 3:
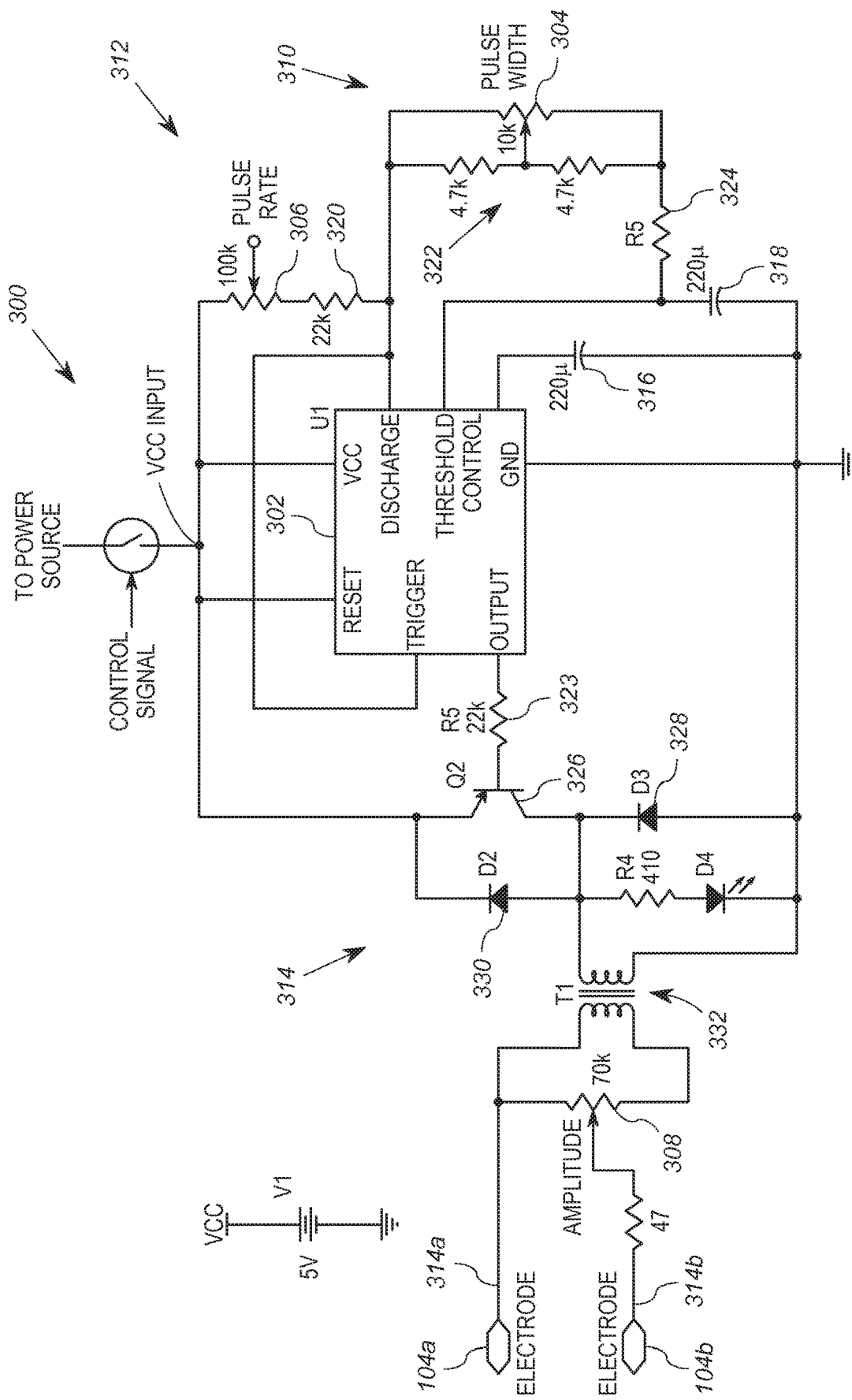
FIG. 3 shows a schematic block diagram of an exemplary stimulation circuit of the arrangement of FIG. 1.

FIG. 3 shows an exemplary stimulation circuit 300 that may be used as the stimulation circuit 112. The stimulation circuit 300 is based on a conventional 555 timer-style integrated circuit ("timer IC") 302, and is configured for manual adjustment via variable resistors 304, 306, and 308. The circuit 300 also includes a VCC input which is operably coupled to the controller 110, a pulse width adjustment circuit 310, a pulse frequency or pulse rate adjustment circuit 312, an output circuit 314, and capacitors 316 and 318. As is known in the art, the timer IC 302 includes a VCC pin, a GND pin, a OUTPUT pin, a RESET pin, a DISCHARGE pin, a THRESHOLD pin, and a CONTROL pin.

The capacitor 316 is coupled between the CONTROL pin and circuit ground. The GND pin is coupled to circuit ground. The capacitor 318 is coupled between the THRESHOLD pin and ground. The VCC input is coupled to the VCC pin. The pulse rate adjustment circuit 312 includes the variable resistor 306 coupled in series with a resistor 320, and is coupled between the VCC input and the DISCHARGE pin. The pulse width adjustment circuit 310 includes two series-coupled resistors 322 coupled in parallel to the adjustable resistor 304, all of which are series connected to another resistor 324. The variable resistor 304 has a variable output coupled to the junction of the series-coupled resistors 322. The pulse width adjustment circuit 310 is coupled between the DISCHARGE pin and the THRESHOLD pin.

The output circuit 314 includes a PNP transistor 326, diodes 328, 330, a transformer 332, and the variable resistor 308. The OUTPUT pin is coupled to the base on the PNP transistor 326 via a resistor 328. The diode 328 is connected in reverse bias from the collector of the PNP transistor 326 to ground, and the diode 330 is connected in forward bias collector to the emitter of the PNP transistor 326. The emitter of the PNP transistor 326 is coupled to the VCC input. The primary winding of the transformer 332 is coupled between the collector of the PNP transistor 326 and circuit ground. The secondary winding of the transformer is coupled across the fixed terminals of the variable resistor 308. The circuit output terminals 314a, 314b are coupled, respectively, to a fixed terminal and the variable resistance terminal of the variable resistor 308. The circuit output terminals 314a, 314b in this example are coupled to a signal electrode 104a and a ground electrode 104b of the one or more electrodes.

The stimulation circuit 300 is configured to generate pulse signals at the output, which propagates to the electrodes 104a, 104b. The variable resistor 304 may be adjusted to a desired pulse width. The variable resistor 306 may be adjusted to a desired pulse rate, and the variable resistor 308 may be adjusted to a desired pulse amplitude. In one embodiment, this circuit 300 may be used in conjunction with ultrasound and other techniques to identify a proper mix of pulse parameters (width, rate, amplitude) that corresponds to the muscles and nerves desired to be stimulated. In some embodiments, the variable resistors 304, 306 and 308 may not be necessary if a uniformly advantageous mix of pulse rate, amplitude and pulse width is employed over a broad spectrum of patients. In other embodiments, one or more variable resistors 304, 306 and 308 are operably coupled to be controlled by control signals of the controller 110, to enable real-time adjustment to the pulse parameters during normal operation. For example, different pulse widths, amplitudes and/or frequencies may be employed depending on the measured IOP values. In such a case, the controller 110 would generate control signals based on the IOP values for one or more of the variable resistors 304, 306, 308.

The pulse signal or other signal may be selected such the electrode acts to reverse the flow of sodium into the eye, or such that the electrode hyperpolarizes the non-pigmented epithelium of the ciliary body.

The pulse signal, which may be replaced by other stimulus signal, may suitably be a periodic pulse signal or a pulse signal having a series of burst pulses with various parameters, such as those disclosed in U.S. patent application Ser. No. 13/941,153, filed Jul. 12, 2013, which is incorporated herein by reference. Alternatively, the stimulation signal may incorporate methods disclosed in the published PCT application serial no. PCT/US2012/061687, filed Oct. 24, 2012, and which is incorporated herein by reference.

In some embodiments, however, the controller 110 only provides control signals that selectively cause voltage to be available at the VCC input. To this end, the VCC input may suitably be coupled to the power source 114 via a switch (e.g. a transistor), not shown, that is controlled by the control signal from the controller 110. Thus, the controller 110 can cause the power source 114 to be selectively coupled to, or decoupled from, the VCC input of the stimulation circuit 300 to selectively operate, or not operate, based on whether the IOP values exceed one or more thresholds, as discussed above.

It will be appreciated that the stimulation circuit 300 is provided by way of example only, and that other circuits that can provide pulse signals (with or without variable pulse width, pulse frequency and pulse amplitude) may be employed. Such other embodiments of the stimulation circuit 300 preferably generate signals using first and ground electrodes 104a, 104b as shown in FIG. 3. For example, it will be appreciated that a single integrated circuit may be employed as both the microcontroller 110 and stimulation circuit 112. In some embodiments, the microcontroller 110 provides the stimulation signal pulse train, which is then merely amplified by the stimulation circuit 112.

Referring again to FIG. 1, the one or more electrodes 104 are operably coupled to receive the stimulation signals from the stimulation circuit 112, and further configured to apply the signals to eye-related tissue. In at least some embodiments, the electrodes 104 are disposed inside the eye and are positioned to modulate the flow of sodium into the eye. In one embodiment, the electrodes 104 are disposed to modulate the release of sodium by the ciliary body into the anterior chamber of the eye. To this end, at least one electrode 104 may be disposed around a nerve proximate to the eye. The nerve, for example, may be the optic nerve, trigeminal nerve, the oculomotor nerve or a branch thereof.

Figure 4:
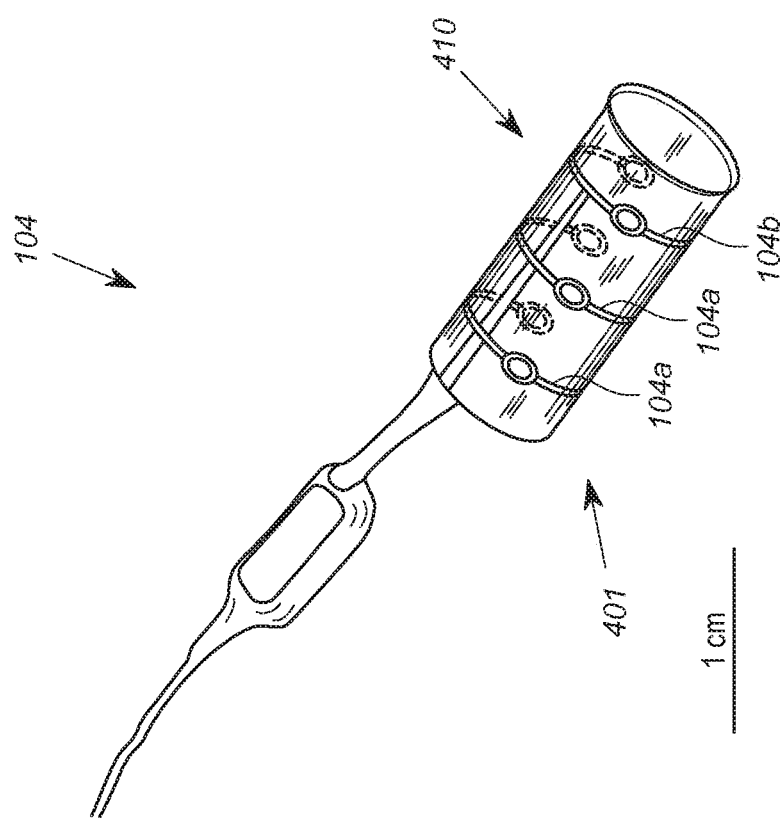
FIG. 4 shows an exemplary set of electrodes affixed to a cuff for use in the arrangement of FIG. 1.

For example, FIG. 4 shows an exemplary embodiment of the electrodes 104 arranged in the form of a probe coupling 401 including a cuff 410 which may be disposed around nerves in or near the eye. The cuff 410 is in the form of a hollow sleeve which allows the cuff 410 to be arranged around the nerve. Disposed around at least portion of the circumference of the cuff 410 are the electrodes 104, which in this embodiment include two signal electrodes 104a and a ground electrode 104b. The electrodes 104 are configured to be electrically coupled to the nerve around which the cuff 410 is disposed. The electrodes 104a, 104b are disposed at different axial positions on the cuff 410.

Figure 5:
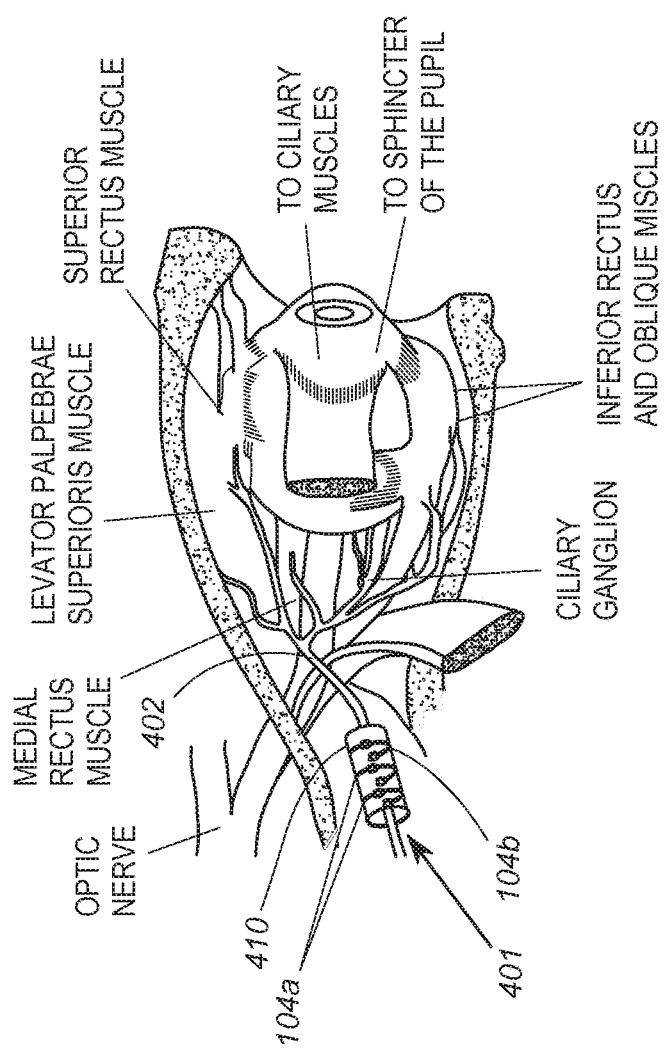
FIG. 5 shows a representative diagram of the set of electrodes and cuff of FIG. 4 implemented in a human eye in a first exemplary arrangement.

As shown in FIG. 5, the cuff 410 of the coupling 401 may be arranged about the oculomotor nerve 402. The cuff 410 may alternatively be disposed about a branch extending from the oculomotor nerve 402. In another case, the electrode 104 may comprise a penetrating electrode that penetrates into the nerve 402, and may be coupled to another type of probe coupling. In any event, the electrode 104 stimulates said nerve 402 to modulate activity in the ciliary body 404.

Figure 6:
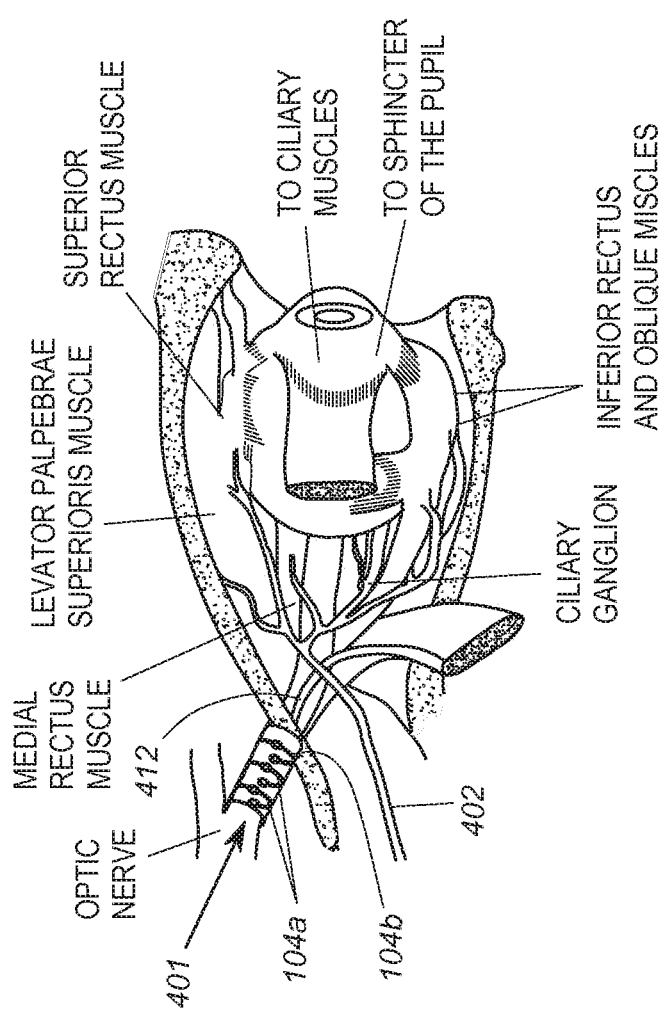
FIG. 6 shows a representative diagram of the set of electrodes and cuff of FIG. 4 implemented in a human eye in a second exemplary arrangement.

FIG. 6 shows another embodiment in which the cuff 410 is disposed about the optic nerve 412 such that the electrode 104 stimulates the optic nerve 412.

Figure 7:
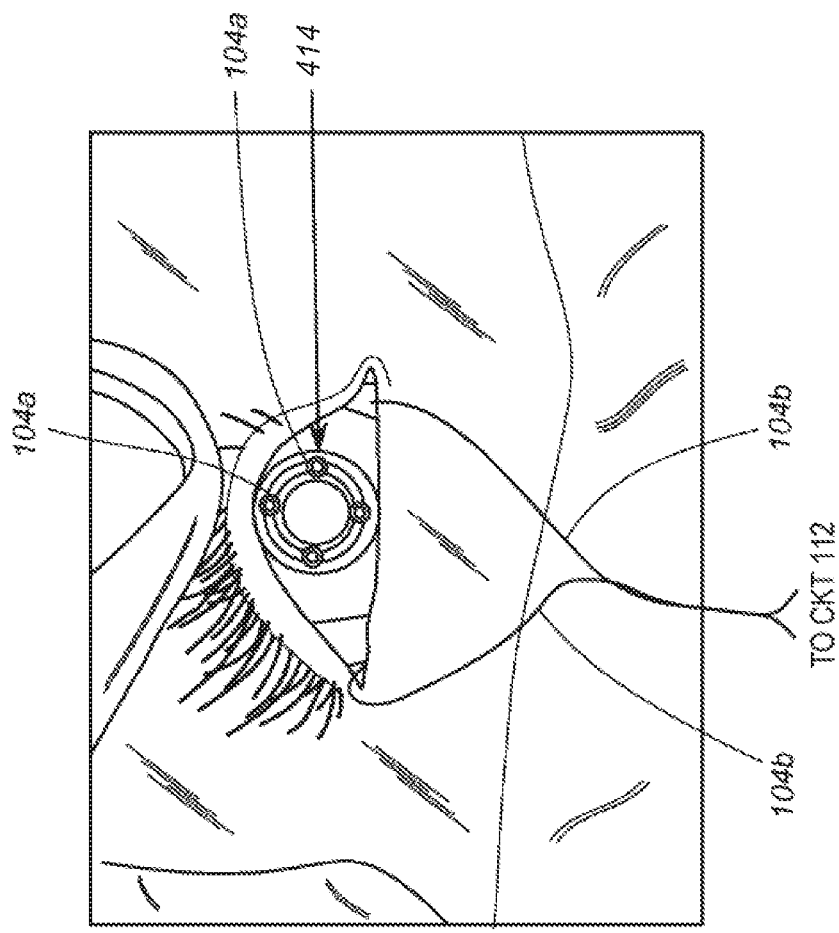
FIG. 7 shows a second exemplary set of electrodes for use in the arrangement of FIG. 1.
Figure 8:
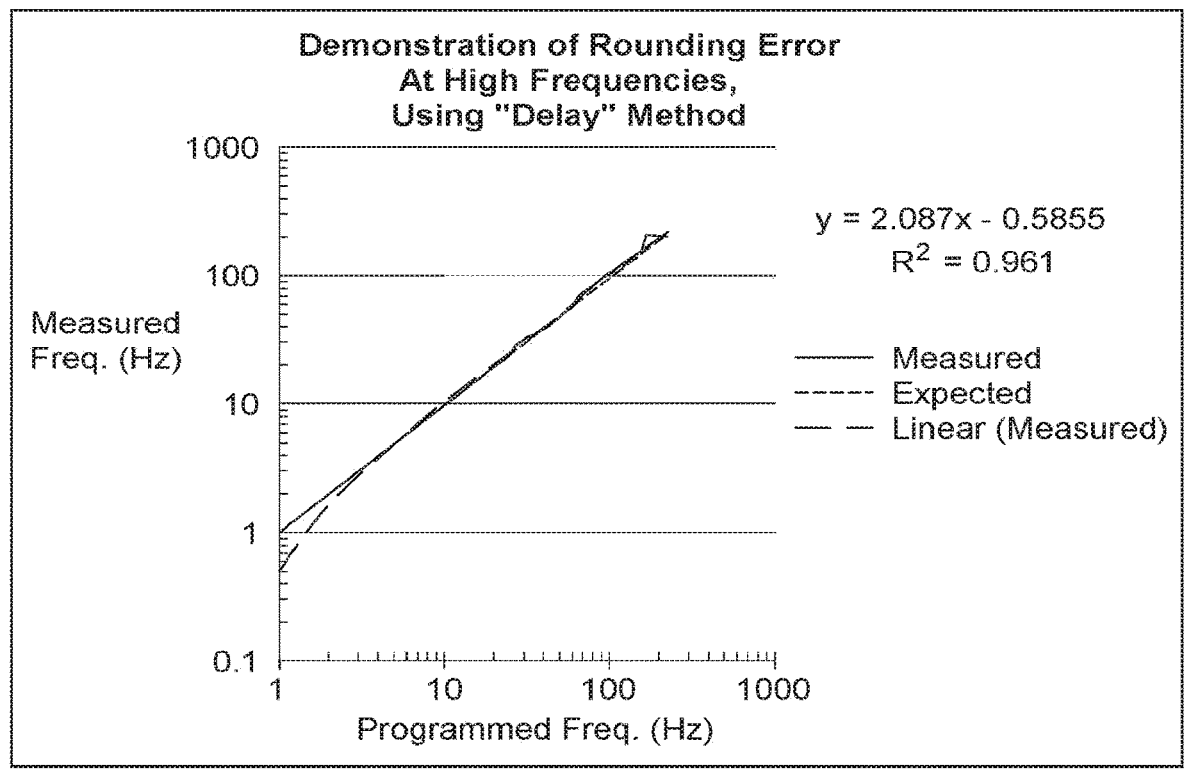
FIG. 8 shows a frequency accuracy chart from an experimental prototype of the arrangement of FIG. 1.
Figure 9:
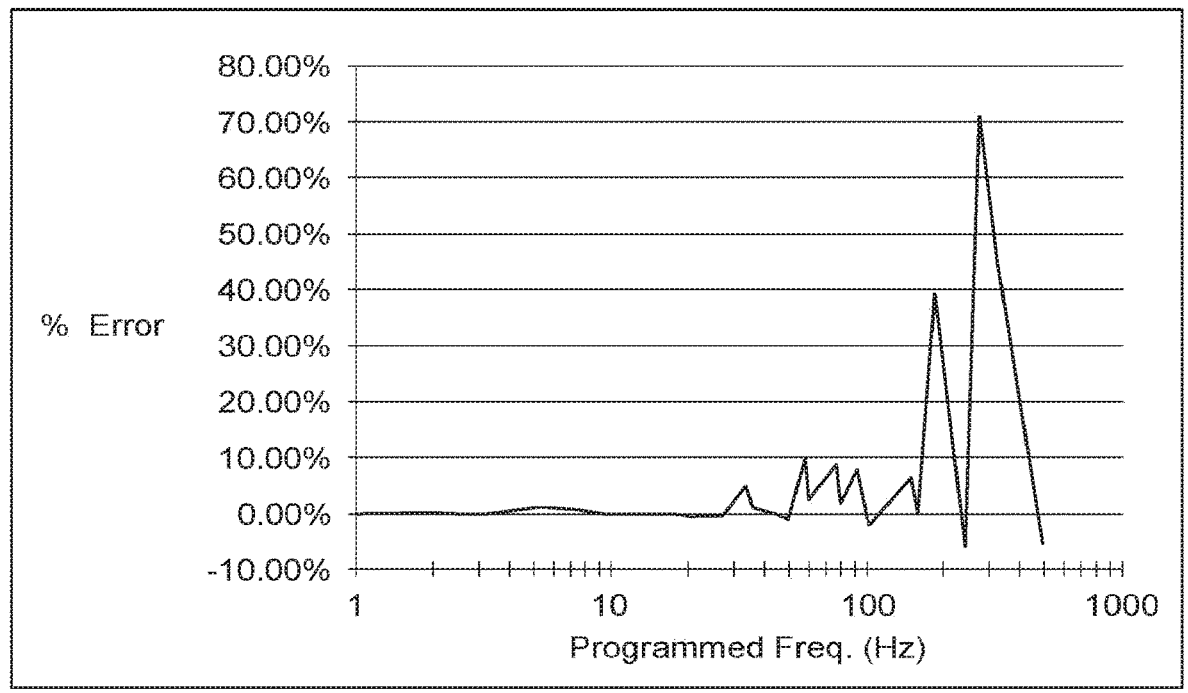
FIG. 9 shows a frequency error chart from an experimental prototype of the arrangement of FIG. 1.
Figure 10:
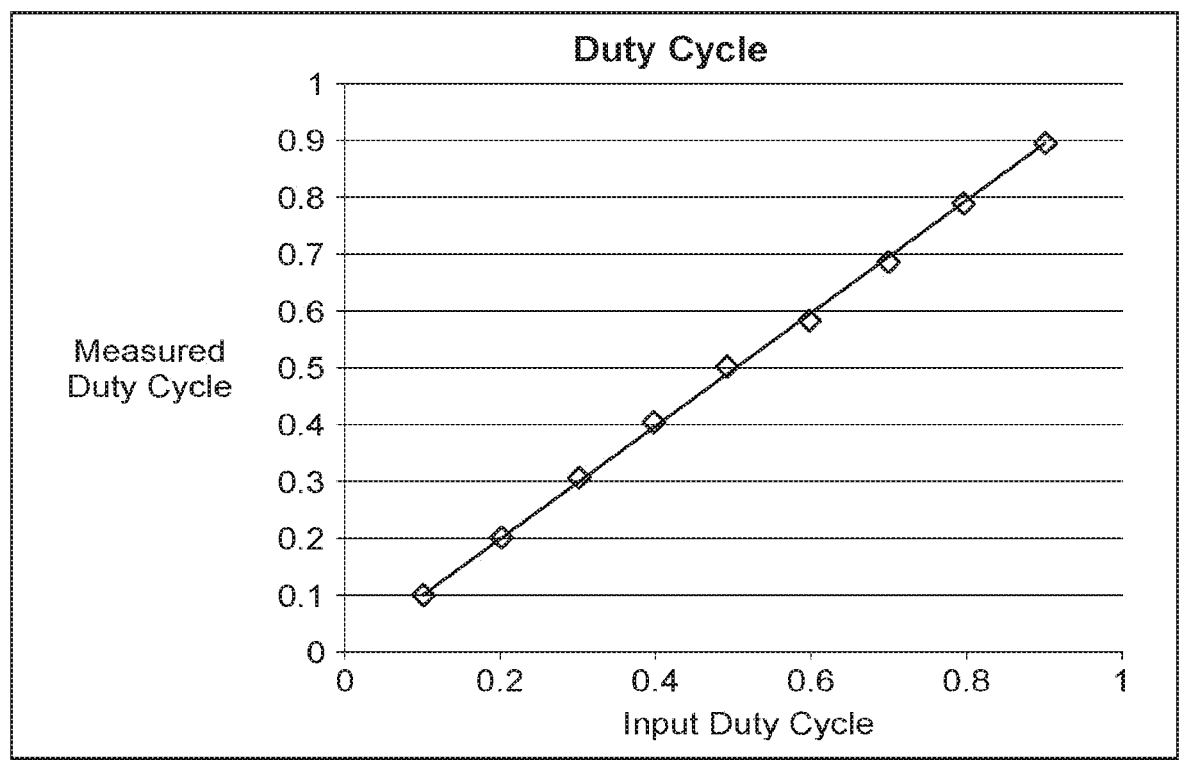
FIG. 10 shows a duty cycle or pulse width accuracy chart from an experimental prototype of the arrangement of FIG. 1.
Figure 11:
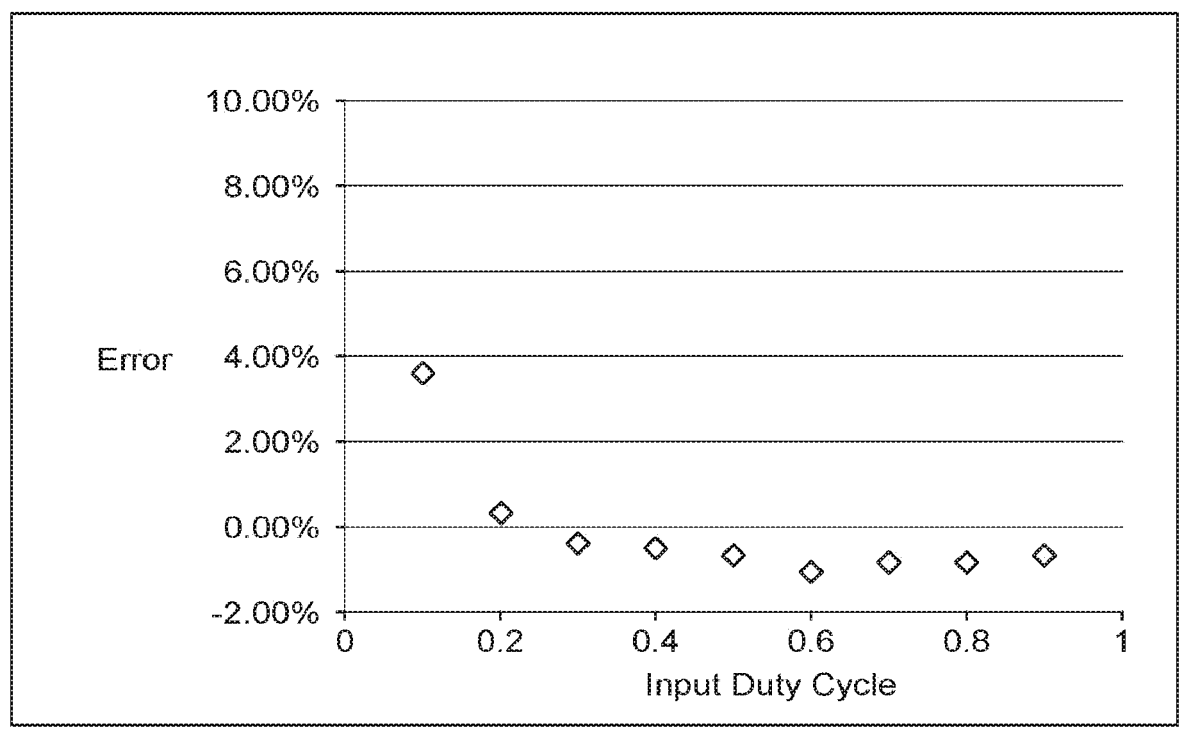
FIG. 11 shows a duty cycle or pulse width error chart from an experimental prototype of the arrangement of FIG. 1.
Figure 12:
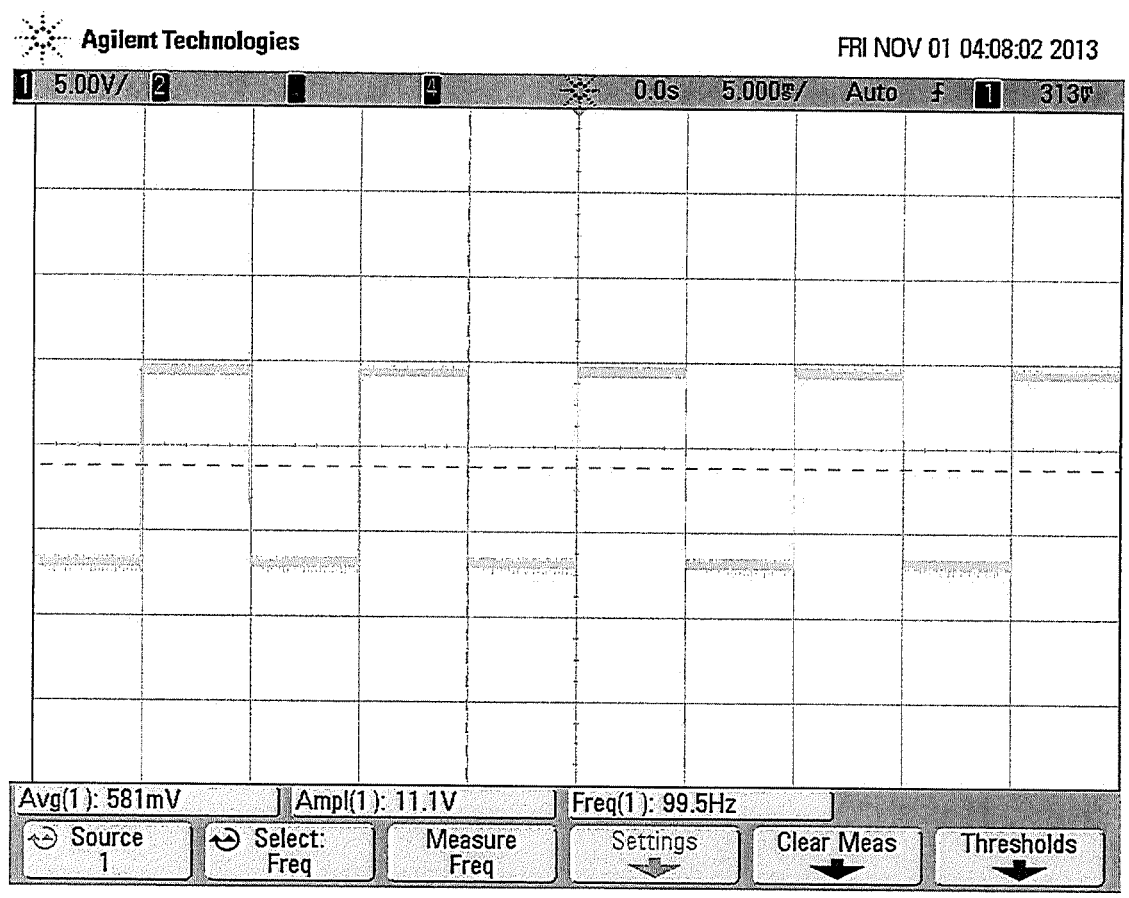
FIG. 12 shows a screen display of an oscilloscope showing a pulse train generated by an experimental prototype of the arrangement of FIG. 1.

In another embodiment, the electrode is disposed in or around the ciliary body of the eye (shown in FIGS. 5 and 6). For example, FIG. 7 illustrates an embodiment of a probe coupling 402 wherein the signal electrode 104a is a ring electrode on a contact lens 414. The contact lens 414 is disposed on the eyeball in a conventional manner, such that the electrode 104a is adjacent to the ciliary body 404. The ground electrode 104b in this case is an HK loop electrode. The electrodes 104a, 104b may in such a position hyperpolarize the non-pigmented epithelium of the ciliary body. The embodiment of FIG. 7 may not have the same level of efficacy of as the embodiment of FIGS. 4 and 5. However, the embodiment of FIG. 7 is non-invasive, and does not require surgery.

In yet other embodiments, the electrode 104 is a ring electrode 104 disposed around the circumference of the eye acting on the ciliary or other nerves and/or drainage tissues. In at least some embodiments, the electrode 104 modulates activity in the ciliary ganglion. Preferably, regardless of where the electrode(s) 104 are coupled, they operate, when subjected to the pulse signal, to stimulate a nerve to modulate activity in the ciliary body. To this end, the electrode is disposed in or around the ciliary body. The electrode modulates the release of sodium by the ciliary body into the anterior chamber of the eye, which is one way to modulate aqueous humor production. Alternatively, or in addition, some embodiments of direct nerve stimulation may modulate nerve activity in the ciliary ganglion, drainage tissues, scleral spur or iris to modulate IOP.

Referring again to FIG. 1, the IOP sensor 108 is a device configured to generate an electrical signal representative of a intraocular pressure. To this end, the IOP sensor 108 may suitably be disposed inside the eye. In another embodiment, the IOP sensor 108 is disposed outside the eye. For example, the IOP sensor 108 may be disposed inside a contact lens, which may suitably be the same contact lens 414 as that in which the electrode 104 is disposed.

Using microcontroller technology, the electrical signal source 102 may be sufficiently small as to be mountable on a pair of eyeglass frames, not shown.

Exemplary details regarding a first prototype of one of the embodiments described above is provided in the following Table 1

TABLE 1

| Subcomponent | Technical Description |
|---|---|
| Power | 5 VDC source |
| Stimulator | 32-162 Hz |
|  | 0-42 V |
| Electrode | 0.5 cm pupil diameter |
|  | 1.3 cm iris diameter |
|  | 36 gauge silver wire |

Electric Field or tissue stimulation may have effect in addition to or independent of direct nerve stimulation. Accordingly, some embodiments can involve stimulation applied close to nerve and not in the nerve itself. The electrodes 104 may therefore stimulate tissue around circumference of eye, around drainage tissues of eye, around the scleral spur, or around ciliary ganglion or ciliary nerves.

Preventions that can be incorporated into the design, such as adding limits to stimulation parameters are the first line of defense and help mitigate negative consequences if the device fails. As well as implementing preventative measures, it is important to be aware of the need for testing, especially of those aspects, such as mechanical lead failure which are difficult to implement preventative measures for. For these aspects, testing and statistical analysis are necessary to quantify the risk, and detection methods need to be made available to the user. Many of these extra tests and measures were not part of the teams original conception of the design. This dedicated analysis provides a structured method to focus on these what-if concerns, potentially increasing the marketability of the device, and preventing serious inconvenience and injury to the user. Much is still unknown about the effectiveness of the device as well as the risk associated with the surgical procedure. After initial surgeries are complete, it will be necessary to account for surgical complications and to make the procedure for the device as simple and safe as possible. There will surely be needed work in mitigation of the surgical risk.

Design Verification Plans for Subcomponent

As discussed above, the microcontroller 110 and stimulation circuit 112 are designed to perform the task of generating a square pulse waveform for electrical stimulation of nerves and muscles. One well established, but bulky device which currently performs this function is the Grass SD9 Square Pulse Stimulator [45]. The compact size, digital control and potential for closed-loop feedback would then push this prototype ahead of currently available muscle stimulators.

The SD9 is rated with 10% accuracy on its stimulation parameters, so this will become the specification for the controlling components of the simulator prototype [45]. For effective therapy, it is important that the stimulator be able to adjust the frequency and duty cycle of the waveform. It is also important that the parameters inputted to the microcontroller result in an accurate output of a waveform with matching characteristics.

Programmed versus measured frequencies and duty cycles can be recorded by inputting a waveform of the specified parameters (swept across the range of interest, 0-500 Hz and 0-100% duty cycle) and then measuring the real waveforms characteristics using an oscilloscope. This will satisfy the design specification for adjustable therapeutic effects.

The SD9 for the prototype is a large, moderately heavy device at 24.1 cm×13.3 cm×14 cm and 1.6 kg [45]. The actual device is smaller and lighter than this model, satisfying the design specification for portability. The weight will be measured by placing the circuit, microcontroller, and electrodes on the scale and measuring in triplicate. The dimensions of the device will be measured using calipers and measured in three dimensions and in triplicate.

Again the SD9 will set the baseline of 10% fidelity for the microcontroller. Since the amplitude of the waveform is not currently controlled digitally (but by an analog potentiometer) it is difficult to determine what the current amplitude is accurately without using an external measuring device, such as a multimeter.

A prototype that was tested is composed of a few major subcomponents. The actual stimulation will be done using an Arduino Uno microcontroller which can manipulate the frequency, pulse width, and amplitude of the stimulation, as well as the total duration. The microcontroller will be controlled using a GUI built from Processing. There were a number of electrodes used to perform the actual stimulation including contact electrodes, HK loop electrodes, DTL fibre electrodes, and cuff electrodes. Rabbits were the animal that stimulation will be tested on and after the first round of surgeries, the optimal parameters of stimulation will be found and used to create the second prototype. This solution is an innovative approach to treating glaucoma by targeting the underlying mechanisms which regulate intraocular pressure using electrical stimulation. The final device incorporates known principles of nerve and muscle stimulation but involves new design in terms of parameters tailored to the intended areas of the eye. Further sophistication has been added by a GUI for controlling parameters which operates through the microcontroller. The microprocessor is also capable of simultaneously recording signal. By avoiding the side effects and need for repeated surgery associated with current treatments, this option aims to provide effective glaucoma relief for those who may have been ineligible for conventional treatment. By targeting the electrical activity directly this therapy also has potential to improve patient outcomes.

Fortunately the Arduino can read voltages, and can be leveraged to act as a multimeter and report the current amplitude to the user, or for use in a control loop. This process is, however subject to error and variation, so the requirements stated will demonstrate whether the device has the appropriate level of accuracy.

The first step into verifying the microcontroller's ability to accurately report voltage is to feed in a known voltage from a function generator and compare the measurements taken using a multimeter to those reported by the Arduinos code. Expected versus measured voltages can then be plotted for the voltage range we are interested in, and a measure of error can be calculated.

The next step was to apply the same procedure with voltages generated by the Arduino. It is possible that in the process of generating waveforms, some error could be introduced to the Arduino's measurements. An input-output curve again can be plotted and the error can be quantified. This is necessary to fulfill the design specification for accurate reporting of stimulation parameters.

The device must deliver the desired range of therapeutic waveforms to ensure the patient is receiving the proper treatment and the patients eyes are not being damaged as per the design specifications. The results we want to achieve are less than 10 mA, 0-15 $V_{pp}$, and average of pulses <100 mV [9] [11].

The procedure for finding these parameters will be using an oscilloscope to measure the output of the circuit across a load and use the oscilloscope functions to find the waveform average and the pulse voltage. An ammeter can be used to find the current.

The operational amplifiers railing level needs to be taken into account to ensure the amplifier performs as desired in the needed ranges. The datasheet by Texas Instruments shows with a ±15V input the expected output is ±14V [46].

It is necessary to make sure that the electrodes are not inhibiting the electrical stimulation of the desired tissues to fulfill our design specification for electrical conductivity. This test both ensures that the parameters that are expected to be delivered are actually delivered, as well as controls the productions of electrodes and allows standardization to occur.

A multimeter will be connected to a positive and ground wire which will be connected to either side of the electrode. The resistance value will then be recorded in triplicate. The average and standard deviation of the resistance will be recorded and the resistances from different electrodes will be compared using t-tests.

We have the design specification for cytotoxity. The agar diffusion test is important for determining if the materials used in our device will cause damage to the cells that they are exposed to. The agar diffusion test uses an agar petri dish with cells and the material being tested placed in the dish. The cells are left to incubate for 24 hours. The petri dish is then studied under a microscope to determine the diameter around the material that the cells do not grow in. The larger the diameter, the greater the toxicity of the material [47] [48].

Localization of stimuli is important to ensure that only the desired tissues are being stimulated so no damage is caused to surrounding tissue. It is also necessary to prevent patient discomfort.

Our goal for determining localization of stimulation is through observations during the rabbit surgeries. If the rabbits head or facial muscles twitch or jerk during stimulation and at no other time, then the electrodes are not localizing the current to the anatomy of the eye we are targeting. Another observation we can make is if there are jumps in the heart rate or spO2 levels. This means that the stimulation is traveling to the heart and lungs causing stimulation in those areas. These are also signs that the electrodes are not localizing the stimulation to the anatomy of the eye. In the future a mathematical model of the charge distribution through stimulation may be helpful in characterizing the anatomical structures that are being affected. These models can use the material properties and shapes of the electrodes as well as those of the eye and surrounding tissue to some extent to determine the flow of charge over time during different stimulation parameters.

It is also necessary to find a non-invasive method to measure IOP reliably and accurately as per the design specification for accuracy of IOP measurement. This cited reference states that researchers used the tono-pen and received measurements with an accuracy of 0:6 mmHg [49]. Accordingly such may be employed as the IOP sensor 108.

The time to successfully initiate stimulation for experienced and inexperienced users will be recorded. This may also develop into a user test that can be taken for certification after a brief training session. A user survey of satisfaction on a scale of 1-10 will also be distributed to determine if the user feels the controls are acceptably easy to use.

The goal of this project is to use electrical stimulation to reduce IOP to treat glaucoma [30]. During the testing on 29 Oct. 2013, this was done measuring IOP changes before and after using simulation as well as using ultrasound to measure flow rates and view anatomical changes within the eye. The procedure consisted of first taking baseline IOP measurement before stimulation in triplicate. The stimulation parameter was then programmed in and applied to the appropriate anatomy. Finally, the IOP was measured in triplicate after stimulation and the change in the mean IOP before and after was calculated. This analysis is performed at a variety of stimulation parameters to determine the optimal input parameters.

The ultrasound measurements determine the effectiveness of IOP measurements in a few ways. One way is in allowing one to view the ciliary body real-time during stimulation. It is critical in initial exploratory testing to determine if the stimulation of various parts of the anatomy are affecting the muscles and flow as is hypothesized. Ultrasound offers a unique way to visualize these changes. Ultrasound also allows the measurement of flow within the eye. It can certainly measure the arterial and venous flow and it may measure the aqueous flow if sensitive enough. Ultrasound will be used before and after stimulation of the ciliary body and before, during, and after oculomotor nerve stimulation. Changes in flow and the anatomy will be recorded and analyzed statistically and qualitatively. While the key measurement is IOP, tonography or other methods may be used to measure drainage, and fluorophotometric methods may be used to measure aqueous production.

The heart rate and oxygen saturation (SpO2) measurements will determine the acute distress of the animal during the procedure. A correlation of the various aspects of the procedure to the time points of the plotted heart rate and SpO2 will determine if some parts of the procedure are more stressful for the animal than others. This data will be most useful when the anesthesia is switched from propofol to isoflurane, as isoflurane is a more consistent form of anesthesia. The procedure will be optimized to minimize stress to the animal by maintaining an elevated spO2 and keeping the heart rate within an acceptable range (140 to 170 bpm).

Design Verification Subcomponent Testing Results

Table 3 shows that although the basic function has been established, some desired specifications were not achieved. Implementing an additional DC blocking capacitor will help improve the performance to achieve the specifications. The results seen in FIGS. 19, 20, 21, 22 and Table 2 show the current prototype meets specifications for adjustable therapeutic effects. The failure of some of the higher frequencies to remain within 10% of the specified value seems to be an artifact of rounding error within the Arduino's delay function, but for the purposes of testing stimulation parameters, having specific low-error frequencies in the upper end of this range is good enough. Further work is being done to allow for more freedom in waveform shape creation including charge-balanced non-symmetric waveforms.

TABLE 2

Table with error of Arduino outputs

| | Error | | Met Specs? |
|---|---|---|---|
| Frequency Fidelity (to programmed value) | Prediction matches measured with $R^2 > .9$ | $R^2$ for regression = 0.961 | Yes |
| Duty Cycle Range | Max error <10% for full duty cycle range | 0%-100% Duty Cycle <4% error | Yes |
| Duty Cycle Fidelity | Prediction matches measured with $R^2 > 0.9$ | $R^2$ for regression = 0.999 | Yes |

TABLE 3

Table for the delivery of the desired range of therapeutic waveforms

| | Specified | Measured | Met Specs? |
|---|---|---|---|
| Current (100 kΩ load) | <10 mA | 0.570 ± 0.007 mA | Yes |
| Voltage (100 kΩ load) | 0-15 $V_{pp}$ | 11.2 ± 0.03 $V_{pp}$ | No |
| Biphasic waveform | <100 $mV_{avg}$ | 581 $mV_{avg}$ | No |

TABLE 4

Arduino frequency range.

| | Specified | Measured | Met Specs? |
|---|---|---|---|
| Frequency Range | 0-500 Hz, Max error <10% for full frequency | 0-170 Hz with <10% Error. 250, 500 Hz <10% | No (Partial Success) |

TABLE 5

Pulse modes from Arduino.

| | Specified | Measured | Met Specs? |
|---|---|---|---|
| Several Pulse Modes | Pulse train, pulse burst, and single pulse modes | Pulse train, pulse burst, and single pulse modes | Yes |

TABLE 6

Amplitude reporting from Arduino.

| | Specified | Measured | Met Specs? |
|---|---|---|---|
| Amplitude Reporting | Max error <10% for 0- | <10% error for 0-9.5 V | Yes, $R^2$ = 0.9998 |

The results for amplitude reporting are promising (Table 6), showing a near-perfect correlation between predicted and measured values allowing us to use the Arduino as a self-monitoring system. The Arduino is, however limited to voltages between 0V and +10V meaning division and or offset will have to be performed to measure a wider range of signals.

Table 7 shows that an op-amp used in connection with the Arduino Uno microcontroller works well in the ranges required, and provides the desired gain.

TABLE 7

Op-amp performance

| | Specified | Measured | Met Specs? |
|---|---|---|---|
| Gain ($V_{in}$ = | 4.3 $V_{pp}$ | 4.25 ± 0.001 $V_{pp}$ | Yes |
| $V_{Rail,upper}$ | $V_{out}$ > | 13.997 ± 0.001 $V_{pp}$ | Yes |
| $V_{Rail,lower}$ | $V_{out}$ < | −12.386 $V_{avg}$± | Yes |

| | Specified | Measured | Met Specs? |
|---|---|---|---|
| Size | 24.1 cm × 13.3 cm × 14 cm | 7.95 cm × 5.33 cm × 4 cm | Yes |
| Weight | 1.6 kg | 56 g | Yes |

Table 8: This shows the device is well within the design specifications for size and weight. Cytotoxicity levels still need to be determined using Agar Diffusion tests (Direct Contact).

TABLE 9

Table of resistances for electrodes [50].

| | Specified | Measured | Met Specs? |
|---|---|---|---|
| HK Loop Electrode | <5 Ω | 0.233 ± 0.058 Ω | Yes, p < 0.0005 |
| Cuff Electrode | <5 Ω | 0.267 ± 0.058 Ω | Yes, p < 0.0005 |
| Corneal Electrode | <5 Ω | 9.97 ± 4.97 Ω | No p = 0.887 |

The resistance values for the HK Loop Electrode and the Cuff Electrode (on table 17) were well below our specifications. The Corneal Electrode was above our specifications. This electrode was bought online, so we may need to adjust our specifications for this electrode. This electrode has also had a bit of injury to it from the initial surgery. The fact that part of the foil has been removed may have caused the increased resistance that is seen in experimentation.

Observations during animal surgeries showed that the stimulation was not localized to the desired tissues. The rabbits facial muscles twitched when stimulation was applied.

The twitches of the rabbits facial muscles indicates that the electrodes did not adequately localize the stimulation to the desired areas. Further investigation needs to be carried out to determine whether the delocalization of stimulation was due to the rupture of gold foil or our corneal electrode.

Baseline IOP: 11:17±0:753 Chi-Squared Analysis: Expected Variance (E)=0.6

Observed Variance (O)=0.753 Chi-Squared value ($x^2$)= 0.0389

TABLE 10

IOP Accuracy design spec.

| | Specified | Measured | Met Specs? |
|---|---|---|---|
| IOP accuracy | Max variance <10% for full frequency range | Variance | Yes, $x^2$ value is less than 0.10 |

Based on the results of this statistical analysis, the IOP measurements taken are accurate enough based on what accuracy has been achieved in the literature. A chi-squared analysis shows the multitude of variance that occurs and based on the value being less than 0.1, there is less than 10% variance.

The surgery time in one implementation was 2.5 hours.

TABLE 11

One sample t-test for IOP changes.

| N | Mean | StDev | SE Mean | 95% C.I. |
|---|---|---|---|---|
| 3 | 7.667 | 1.528 | 0.882 | (3.872, 11.461) |

TABLE 12

IOP change after stimulation

| | Specified | Measured | Met Specs? |
|---|---|---|---|
| IOP change after stimulation | IOP change >0 | ΔIOP | Yes, 0 change is outside the 95% C.I. |

This study provides an initial result. In the first surgery there were many unknown variables that were accounted for which caused less than perfect results. The initial results indicated that the stimulation does seem to be changing the IOP by a statistically significant amount.

Design Verification for Final Prototype

The immunological response to the device in the eye is an important indicator in how much harm the electrode itself and the stimulation are causing to the surface of the cornea. This consideration will be accounted for by measuring the corneal thickness before and after stimulation using ultrasound. The corneal thickness is an indicator of inflammation of the eye before and after stimulation. Ultrasound measurement offers an extremely precise measurement method. The corneal thickness before and after stimulation will be measured in the stimulated eye and the other eye (control eye) to determine if there is a statistical difference in the corneal thickness due to the electrode and stimulation.

The agar diffusion test is important for determining if the materials used in our device will cause damage to the cells that they are exposed to. The agar diffusion test uses an agar petri dish with cells and the material being tested placed in the dish. The cells are left to incubate for 24 hours. The petri dish is then studied under a microscope to determine the diameter around the material that the cells do not grow in. The larger the diameter, the greater the toxicity of the material [47].

Measuring the waveforms entering the eye is necessary information to know so we are aware exactly what is being applied to the eye. This is done by using the Arduino as a multimeter.

For the safety of the patient, it is critical to ensure the sterility of the electrodes before the procedure. Sterilization can be performed through gamma rays or EtOH, but the most convenient and prevalent method is autoclaving. The electrodes used in the procedure undergo autoclaving for two reasons. The first reason is to determine if the electrodes are mechanically sound enough to endure the harsh method of autoclaving. This will be determined by physical inspection of the electrodes as well as electrical characteristic testing. The second reason is to determine if the electrodes are sterilized by the autoclaving. This will be determined by a bacterial growth test by swabbing the electrodes after autoclaving and seeing if anything from them will grow.

It is important to make sure that the device does not inhibit vision while wearing it, but it is also important to make sure that the stimulation does not cause immediate vision trouble or chronic vision trouble. To ensure that our device does not affect vision, a visual acuity test is performed before, during, and after device has been applied. The acuity test before the device will yield a base score. The tests during will tell us if the device is inhibiting vision due to the materials used or because of the stimulation. The test after will indicate that the stimulation does not have chronic effects. The test is performed by placing the chart 20 feet away from the patient and asking them to read the smallest line.

The device is currently undergoing trials in the rabbit animal model to examine how well it reduces intraocular pressure. These experiments involve the following steps (but a more indepth procedure can be found by examining the surgical logs):

Anesthetize the rabbit, establish a running IV drip of anesthesia

Measure baseline levels of IOP before any treatment, then again with electrodes in place, but with no stimulation.

Stimulation would then be administered through the arduino and circuit, controlled by a laptop.

IOP is then triple sampled 5 seconds after the predetermined end of stimulation.

Not only are we interested in the ability of the device to lower IOP in the rabbit, but also that the magnitude of therapy (the reduction in pressure) is adjustable to several levels. The severity of glaucoma will vary between patients and over time, therefore there is a customer need for the device to adapt therapy levels. This will be tested using an addition the above procedure wherein parameters of stimulation will be chosen at levels predicted to provide intermediate IOP changes. Statistical analysis will then be performed on the results that would confirm or deny that several levels of therapeutic effect are achievable.

This product is intended for use in the reduction of intraocular pressure in patients with open-angle glaucoma, as well as other types of glaucoma and/or ocular hypertension (OHT) through the principles of Neuromuscular Electrical Nerve Stimulation (LAMES) on the surface of the eye, ocular motor nerve, ciliary nerves and optic nerve [51] [52] [53].

REFERENCES

[1] G. R. Foundation, "Glaucoma facts and stats," 2013, August, available: http://www.glaucoma.org/glaucoma/glaucoma-facts-and-stats.php.

[2] Mayo Clinic Staff, "Glaucoma: Treatment and drugs," 2012, October, available: www.mayoclinic.com/health/glaucoma/DS00283/DSECTION=treatments-and-drugs.

[3] Managed Care Eye Institute, "Coats of the eye: Ciliary body," available: http://teaching.pharmacy.umn.edu/courses/eyeAP/EyeAnatomy/CoatsoftheEye/Ciliary-Body.htm.

[4] E. Janunts, "Optical remote sensing of intraocular pressure by an implantable nanostructured array," available: http://www.uniklinikum-saarland.de/en/facilities/departments and institutes/experimental ophthalmology/research/iop sensing/.

[5] J. Porcari, K. Palmer McLean, C. Foster, T. Kernozek, B. Crenshaw, and C. Swenson, "Electrical muscle stimulation on body composition, muscle strength, and physical appearance," Journal of Strength and Conditioning Research, vol. 16, pp. 165-172, 2002.

[6] B. Braendstrup, "Muscular bio stimulator (2nd version)," 2011, May, available: http://www.redcircuits.com/Page124.htm.

[7] I. Constable and A. Lim, Color Atlas of Ophthalmology. World Scientific Publishing Company, 1995.

[8] H. Murgatroyd and J. Bembridge, \Intraocular pressure," Oxford Journal of Medicine, vol. 8, pp. 100-103, 2008.

[9] A. Nesterov and E. Khadikova, "Effect of ciliary muscle electrical stimulation on ocular hydrodynamics and visual function in patients with glaucoma," Vestn Oftalmol., vol. 113, pp. 12-14, 1997, available: http://www.ncbi.nlm.nih-.gov/pubmed/9381633.

[10] M. Filippello, "System for preventing of trearting open angle glaucoma and presbyopia," June 2009, available: http://www.google.com/patents/WO2009150688A2?cl=en.

[11] H. Friedman, "Electro-ocular stimulation system," August 1981, available: http://www.google.com/patents/US4271841.

[12] W. Kamerling, "System for preventing of treating open angle glaucoma and presbyopia," August 1986, available: http://www.google.com/patents/US4603697.

[13] L. Vorvick, "Glaucoma," September 2011, available: http://www.nlm.nih.gov/medlineplus/ency/article/001620.htm.

[15] H. Quigley and S. Vitale, "Models of open-angle glaucoma prevalence and incidence in the united states," Investigative Ophthalmology and Visual Science, vol. 38, January 1997, available: http://www.ncbi.nlm.nih.gov/pubmed/9008633.

[16] T. Dietlein, "The medical and surgical treatment of glaucoma," Dtsch Arztebl Int, vol. 116, pp. 597-606, 2009.

[17] H. Kok and K. Barton, "uveitic glaucoma," Ophthalmol Clin North Am, vol. 15, pp. 375-387, 2002.

[18] R. Van der Valk, "Intraocular pressure-lowering effects of all commonly used glaucoma drugs: a meta-analysis of randomized clinical trials," Ophthalmology, vol. 112, pp. 1177-1185, 2005.

[19] R. Moorthy, "Glaucoma associated with uveitis," Sury Ophthalmol, pp. 361-394, 1997.

[20] M. Shields, Shields textbook of glaucoma. Philadelphia, Pa.: Lippincott Williams & Wilkins, 2005.

[21] U. Z. Leuven, "Validation of retinal oximetry in glaucoma patients: a structural and functional correlation,' February 2013, available: http://www.clinicaltrials.gov/ct2/show/NCT01391247?term=glaucoma&rank=13.

[22] V. E. S. Center, "Ahmed valve glaucoma implant with adjunctive subconjunctival bevacizumab in refractory glaucoma," May 2010, available: http://www.clinicaltrials.gov/ct2/show/NCT01128699?term=glaucoma&rank=15.

[23] D. Epstein, P. Lee, and R. Vasanth, "Method of preventing of treating glaucoma," January 2007, available: http://www.uspto.gov/web/patents/patog/week15/OG/html/1389-2/US0841536420130409.html.

[24] C. Euteneuer, T. Hektner, A. Schieber, and J. Wardle, "Methods and apparatus for treating glaucoma," March 2009, available: http://www.uspto.gov/web/patents/patog/week38/OG/html/1382-3/US08267882-20120918.html.

[25] C. Euteneuer, T. Hektner, and A. Schieber, "Glaucoma treatment method," May 2010, available: http://www.uspto.gov/web/patents/patog/week41/OG/html/1383-2/US08282592-20121009.html.

[26] M. Rickard, "Glaucoma drainage device with pump," July 2010, available: http://www.uspto.gov/web/patents/patog/week16/OG/html/1389-3/US08419673-20130416.html.

[27] D. Castillejos, "Method and intra sclera implant for treatment of glaucoma and presbyopia," August 2002, available: http://www.uspto.gov/web/patents/patog/week38/OG/html/1382-3/US08267995-20120918.html.

[28] Mountaintop Medical, "Advances in opthamolgy: Markets in the treatment of eye disorders and corrective vision," July 2009, available: http://academic.marketresearch.com/product/display.asp?productid=2271479&curl=&surl=%2Fsearch%2Fresults%2Easp%3Fprid%3D872210188%26query%3Dglaucoma%26cmdgo%3DGo&prid=872210188.

[29] G. Chandler, "Key needs and opportunities for treating glaucoma," Investigative Ophthalmology and Visual Science, vol. 53, May 2012, available: http://www.iovs.org/content/53/5/2456.full.

[30] A. King, "Clinical review: Glaucoma,' BMJ, vol. 346, 2013.

[31] M. Ghosh, T. Kiang, and M. Eydelman, "Lens—solution interactions: Impact on biocompatibility," in The 15th Symposium on the Material Science and Chemistry of Contact Lenses. Center for Devices and Radiological Health, FDA, 2011, March, available: http://www.fda.gov/downloads/AboutFDA/CentersOffices/CDRH/CDRHFOIAElectronicReadingRoom/UCM279425.pdf.

[32] M. Detry-Morel, "Side effects of glaucoma medications," Bull. Soc. Belge Ophthal., vol. 299, pp. 27-40, 2006.

[33] P. Foster, "Specific questions related to glaucoma," available: http://www.rcophth.ac.uk/page.asp?section=373&sectionTitle=Specific+Questions+Related+to+Glaucoma.

[34] Glaucoma Research Foundation, "Laser surgery," 2013, June, available: http://www.glaucoma.org/treatment/laser-surgery.php.

[35] John M. Eisenberg Center for Clinical Decisions and Communications Science, "Treatments for open-angle glaucoma," AHRQ, vol. 12, 2013.

[36] R. Fernandes, B. Diniz, R. Ribeiro, and M. Himayun, "Artificial vision through neuronal stimulation," Neuroscience Letters, vol. 519, pp. 122-128, 2012.

[37] US Food and Drug Administration, "Classify your medical device," 2012, December, available: http://www.fda.gov/MedicalDevices/DeviceRegulationandGuidance/Overview/ClassifyYourDevice/.

[38] C. Greenwell and D. Spillman, "Use of medicated drops and oral tablets in glaucoma treatment," Curr Opin Ophthalmol., vol. 7, pp. 44-46, April 1996, available: http://www.ncbi.nlm.nih.gov/pubmed/?term=medicated+eye+drops+for+glaucoma.

[39] J. Lee, B. Wong, D. Yick, I. Wong, C. Yuen, and J. Lai, "Primary acute angle closure: long-term clinical outcomes over a 10 year period in the chinese population," June 2013, preprint, Available: http://www.ncbi.nlm.nih.gov/pubmed/23733280.

[40] F. Parisi, N. Pescosolido, P. Russo, G. Buomprisco, and M. Nebbioso, "Role of dopaminergic receptors in glaucomatous disease modulation," Biomed. Res. Int., 2013, available: http://www.ncbi.nlm.nih.gov/pubmed/23878797.

[41] H. Wang, N. Wang, and S. Li, "Intervention of laser periphery iridectomy to posterior iris bowing in high myopic eyes," Chin. Med. J. (Engl)., vol. 125, pp. 4466-4469, December 2012, available: http://www.ncbi.nlm.nih.gov/pubmed/23253721.

[42] J. Panarelli, M. Banitt, and P. Sidoti, "Scleral stula closure at the time of glaucoma drainage device tube repositioning: a novel technique," Arch Ophthalmol., vol. 130, pp. 1447-1451, November 2012, available: http://www.ncbi.nlm.nih.gov/pubmed/23143444.

[43] H. Fechter, "Improvised 3-0 polypropylene plug for the glaucoma drainage tube during phacoemulsification," Ophthalmic. Surg. Lasers Imaging., vol. 39, pp. 86-87, January-February 2008, available: http://www.ncbi.nlm.nih.gov/pubmed/18254361.

[44] Y. Yan, Y. Lu, X. Chai, Q. Ren, Y. Chen, and L. Li, "Electrical stimulation with a penetrating optic nerve electrode array elicits visuotopic cortical responses in cats." J Neural Eng., vol. 10, June 2013, available: http://www.ncbi.nlm.nih.gov/pubmed/23665847.

[45] G. Technologies, "Sd9 square pulse stimulator," 2013, available: http://www.grasstechnologies.com/products/stimulators/stimsd9.html.

[46] T. Instruments, "Lm741 operational amplifier," March 2013, available: http://www.ti.com/lit/ds/symlink/lm741.pdf.

[47] FDA, "Guidance for industry and for fda reviewers/staff-guidance on 510(k) submissions for keratoprostheses," March 1999, available: http://www.fda.gov/medicaldevices/deviceregulationandguidance/guidancedocuments/ucm073785.htm.

[48] I. Lewinstein, S. Matalon, S. Slutzkey, and E. Weiss, "Antibacterial properties of aged dental cements evaluated by direct-contact and agar diffusion tests," Journal of Prosthetic Dentistry, vol. 93, pp. 364-371, April 2005, available: http://www.thejpd.org/article/S0022-3913(05)00041-7/abstract.

[49] A. Kobayashi, T. Yoshita, and Y. Shirao, "Accuracy of intraocular pressure by tono-pen xl over amniotic membrane patching in rabbits," American Journal of Ophthalmology, vol. 135, pp. 536-537, April 2003, available: http://www.ajo.com/article/S0002-9394(02)02051-2/abstract.

[50] V. Wong and S. Graham, "Effect of repeat use and coating defects of gold foil electrodes on electroretinogram recording," Vision Research, vol. 35, pp. 2795-2799, October 1995, available: http://www.sciencedirect.com/science/article/pii/0042698995000463.

[51] Tomey Corporation, "Tomey dtl electrode," May 1997, available: http://www.accessdata.fda.gov/cdrh_docs/pdf/K961805.pdf.

[52] Optonol Ltd., "Summary of safety & effectiveness," March 2003, available: http://www.accessdata.fda.gov/cdrh_docs/pdf3/K030350.pdf.

[53] A. Keenan, "510(k) summary," November 2008, available: http://www.accessdatafda.gov/cdrhdocs/pdf8/K082011.pdf.

[54] X. Pham and J. Hu, "Cytotoxicity evaluation of multipurpose contact lens solutions using an in vitro test battery," CLAO Journal, vol. 25, January 1999, available: http://journals.lww.corn/claojournal/abstract/1999/01000/cytotoxicity_evaluation_of_multipurpose_contact.9.aspx.

[55] G. Sjogren and G. S. J. Dahl, "Cytotoxicity of dental alloys, metals, and ceramics assessed by millipore filter, agar overlay, and mtt tests," Elsevier, vol. 84, August 2000, available: http://www.sciencedirect.com/science/article/pii/S0022391300041895.

[56] FDA, "Draft guidance for industry and fda staff: Class ii special controls guidance document: Powered muscle stimulator for rehabilitation," April 2010, available: http://www.fda.gov/MedicalDevices/DeviceRegulatio-nandGuidance/GuidanceDocuments/ucm198793.htm.

[57] J. Sun, Y. Lu, P. Cao, X. Li, C. Cai, X. Chai, Q. Ren, and L. Li, "Spatiotemporal properties of multipeaked electrically evoked potentials elicited by penetrative optic nerve stimulation in rabbits," Investigative Ophthalmology and Visual Science, vol. 52, August 2010, available: http://www.iovs.org/content/52/1/146.long.

[58] A. Ahmed, "Addendum viii," November 1993, available: http://www.accessdata.fda.gov/cdrhdocs/pdf/K925636.pdf.

[59] Optonol Ltd., "510(k) summary," March 2002, available: http://www.accessdata.fda.gov/cdrhdocs/pdf/K012852.pdf.

What is claimed is:

1. A system for reducing intraocular pressure within an anterior chamber of a mammalian eye, comprising:
    a contact lens configured to be positioned on an exterior surface of the mammalian eye and comprising at least one ring electrode configured to be positioned adjacent to a ciliary body of the mammalian eye when the contact lens is positioned on an exterior surface of the mammalian eye; and
    a stimulation signal source coupled to the contact lens, the stimulation signal source comprising a microcontroller configured to provide control signals and a stimulation circuit configured to generate a pulsed electrical signal in response to control signals from the microcontroller, wherein the stimulation circuit is configured to apply the pulsed electrical signal to the at least one ring electrode when positioned adjacent to the ciliary body of the mammalian eye, and
    wherein the electrical signal causes a release of sodium by the ciliary body into the anterior chamber of the mammalian eye to thereby reduce the intraocular pressure within the anterior chamber of the mammalian eye.

2. The system of claim 1, wherein the at least one ring electrode is configured to be disposed adjacent to a nerve associated with the ciliary body of the mammalian eye.

3. The system of claim 1, wherein the at least one ring electrode is disposed on or in the contact lens.

4. The system of claim 1, wherein the stimulation signal source is sized and configured to be mounted on a pair of eye-glasses frames.

5. The system of claim 1, wherein the at least one ring electrode is configured to be disposed in or around the ciliary body such that the at least one ring electrode hyperpolarizes the non-pigmented epithelium of the ciliary body of the mammalian eye.

6. The system of claim 1, further comprising a sensor coupled to the stimulation signal source and configured to measure an intraocular pressure of the mammalian eye, wherein the stimulation signal source provides the pulsed electrical signal to the at least one ring electrode in response to the intraocular pressure measurement.

7. The system of claim 6, wherein the sensor is disposed outside the eye.

8. The system of claim 6, wherein the sensor is disposed inside the contact lens.

9. A system for reducing intraocular pressure within an anterior chamber of a mammalian eye, comprising:
    means for positioning at least one ring electrode on an exterior surface of the mammalian eye adjacent to a ciliary body of the mammalian eye; and
    means for providing control signals and generating a pulsed electrical signal in response to control signals, wherein the means for generating the pulsed electrical signal is configured to apply the pulsed electrical signal to the at least one ring electrode when positioned adjacent to the ciliary body of the mammalian eye, and
    wherein the electrical signal causes a release of sodium by the ciliary body into the anterior chamber of the mammalian eye to thereby reduce the intraocular pressure within the anterior chamber of the mammalian eye.

10. The system of claim 9, wherein the at least one ring electrode is configured to be disposed adjacent to a nerve associated with the ciliary body of the mammalian eye.

11. The system of claim 9, wherein the at least one ring electrode is disposed on or in a contact lens.

12. The system of claim 9, wherein the means for providing control signals is sized and configured to be mounted on a pair of eye-glasses frames.

13. The system of claim 9, wherein the at least one ring electrode is configured to be disposed in or around the ciliary body such that the at least one ring electrode hyperpolarizes the non-pigmented epithelium of the ciliary body of the mammalian eye.

14. The system of claim 9, further comprising means for measuring an intraocular pressure of the mammalian eye, wherein the pulsed electrical signal is provided to the at least one ring electrode in response to the intraocular pressure measurement.

15. The system of claim 14, wherein the means for measuring an intraocular pressure is disposed outside the eye.

16. The system of claim 14, wherein the means for measuring an intraocular pressure is disposed inside a contact lens.

17. A system for reducing intraocular pressure within an anterior chamber of a mammalian eye, comprising:
    a contact lens configured to be positioned on an exterior surface of the mammalian eye and comprising at least one ring electrode configured to be positioned adjacent to a ciliary body of the mammalian eye when the contact lens is positioned on an exterior surface of the mammalian eye, the contact lens comprising a sensor configured to measure an intraocular pressure of the mammalian eye; and
    a pair of eye-glasses frames comprising a stimulation signal source coupled to the contact lens, the stimulation signal source comprising a microcontroller configured to provide control signals and a stimulation circuit configured to generate a pulsed electrical signal in response to control signals from the microcontroller, wherein the stimulation signal source provides the pulsed electrical signal to the at least one ring electrode in response to the intraocular pressure measurement,
    wherein the stimulation circuit is configured to apply the pulsed electrical signal to the at least one ring electrode when positioned adjacent to the ciliary body of the mammalian eye, and
    wherein the electrical signal causes a release of sodium by the ciliary body into the anterior chamber of the mammalian eye to thereby reduce the intraocular pressure within the anterior chamber of the mammalian eye.

18. The system of claim 17, wherein the at least one ring electrode is configured to be disposed adjacent to a nerve associated with the ciliary body of the mammalian eye.

19. The system of claim 17, wherein the at least one ring electrode is disposed on or in the contact lens.

20. The system of claim 17, wherein the at least one ring electrode is configured to be disposed in or around the ciliary body such that the at least one ring electrode hyperpolarizes the non-pigmented epithelium of the ciliary body of the mammalian eye.

* * * * *